US008663607B2

(12) United States Patent
Monzyk et al.

(10) Patent No.: US 8,663,607 B2
(45) Date of Patent: Mar. 4, 2014

(54) FERRATE(VI)-CONTAINING COMPOSITIONS AND METHODS OF USING FERRATE(VI)

(75) Inventors: Bruce F. Monzyk, Delaware, OH (US); Michael J. Murphy, Dublin, OH (US); Chad Cucksey, Worthington, OH (US); F. Michael von Fahnestock, Columbus, OH (US); Andrew J. Savage, Dublin, OH (US); David N. Clark, Los Lunas, NM (US)

(73) Assignee: Battelle Memorial Institute, Columbus, OH (US)

( * ) Notice: Subject to any disclaimer, the term of this patent is extended or adjusted under 35 U.S.C. 154(b) by 625 days.

(21) Appl. No.: 12/529,540

(22) PCT Filed: Mar. 10, 2008

(86) PCT No.: PCT/US2008/056446
§ 371 (c)(1),
(2), (4) Date: Mar. 5, 2010

(87) PCT Pub. No.: WO2008/112657
PCT Pub. Date: Sep. 18, 2008

(65) Prior Publication Data
US 2011/0268672 A1   Nov. 3, 2011

Related U.S. Application Data

(60) Provisional application No. 60/893,929, filed on Mar. 9, 2007, provisional application No. 60/946,134, filed on Jun. 25, 2007, provisional application No. 60/946,940, filed on Jun. 28, 2007.

(51) Int. Cl.
| A61K 8/21 | (2006.01) |
| A61K 8/30 | (2006.01) |
| A61Q 11/00 | (2006.01) |
| A61K 8/00 | (2006.01) |
| A61K 8/18 | (2006.01) |
| A01N 59/16 | (2006.01) |
| A61K 33/26 | (2006.01) |
| C11D 3/20 | (2006.01) |
| C11D 17/00 | (2006.01) |
| C11D 3/37 | (2006.01) |

(52) U.S. Cl.
USPC ............... 424/52; 424/49; 424/646; 510/109; 510/191; 510/276

(58) Field of Classification Search
None
See application file for complete search history.

(56) References Cited

U.S. PATENT DOCUMENTS

| 3,372,125 A | 3/1968 | Hill |
| 3,704,227 A * | 11/1972 | Hill ............................... 510/117 |
| 3,904,421 A | 9/1975 | Shimizu et al. |
| 4,156,613 A | 5/1979 | Hund |
| 4,225,352 A | 9/1980 | Makino et al. |
| 4,243,494 A | 1/1981 | Riggs, Jr. et al. |
| 4,256,551 A | 3/1981 | Cliff et al. |
| 4,606,843 A | 8/1986 | Kaczur |
| 4,705,726 A | 11/1987 | Shindou et al. |
| 5,284,642 A | 2/1994 | Evrard et al. |
| 5,416,150 A | 5/1995 | Boeck |
| 5,607,504 A | 3/1997 | Schmid et al. |
| 6,080,288 A | 6/2000 | Schwartz et al. |
| 6,267,896 B1 | 7/2001 | Patterson et al. |
| 6,471,788 B1 | 10/2002 | Minevski et al. |
| 6,566,574 B1 | 5/2003 | Tadros et al. |
| 6,576,346 B1 | 6/2003 | Ravenscroft et al. |
| 6,723,890 B2 | 4/2004 | Tucker et al. |
| 6,837,984 B2 | 1/2005 | Wang et al. |
| 6,899,769 B2 | 5/2005 | Ravenscroft et al. |
| 6,899,956 B2 | 5/2005 | Block et al. |
| 7,045,024 B2 | 5/2006 | Minevski et al. |
| 7,045,051 B2 | 5/2006 | Minevski et al. |
| 7,291,217 B2 | 11/2007 | Phelps et al. |
| 7,347,893 B2 | 3/2008 | Low |
| 7,387,671 B2 | 6/2008 | Meisen et al. |
| 7,387,672 B2 | 6/2008 | Friedrich |
| 7,410,536 B2 | 8/2008 | Friedrich et al. |
| 7,422,793 B2 | 9/2008 | Phelps et al. |
| 2002/0098989 A1 | 7/2002 | Heimann et al. |
| 2003/0042134 A1 | 3/2003 | Tremblay et al. |
| 2003/0055245 A1 | 3/2003 | Tseng et al. |
| 2003/0124065 A1 * | 7/2003 | Majeti et al. .................... 424/49 |
| 2003/0146169 A1 | 8/2003 | Ciampi et al. |
| 2003/0159942 A1 | 8/2003 | Minevski et al. |
| 2004/0104377 A1 | 6/2004 | Phelps et al. |
| 2004/0216637 A1 | 11/2004 | Buchheit et al. |

(Continued)

FOREIGN PATENT DOCUMENTS

| CN | 1524595 | 9/2004 |
| DE | 553004 | 5/1943 |

(Continued)

OTHER PUBLICATIONS

Svanks, "Oxidation of Ammonia in Water by Ferrates (VI) and (IV)", Project Completion Report No. 444, Jun. 1976.*

Audette, R.J., Quail, J.W.: "Potassium, Rubidium, Cesium, and Barium Ferrates(VI). Preparations, Infrared Spectra, and Magnetic Susceptibilities". Inorganic Chemistry, [Online], vol. 11, No. 8, Aug. 1972, XP002569971 DOI: 10.1021/ic50114a034 [retrieved on Feb. 23, 2010].

Bouzek, K., Lipovska, M., Schmidt, M., Rousar, I., Wragg, A.A.: "Electrochemical Production of Ferrate(VI) Using Sinusoidal Alternating Current Superimposed on Direct Current: Grey and White Cast Iron Electrodes". Electrochimica Acta, vol. 44 (1998) pp. 547-557.

Bouzek, K., Rousar, I.: "The Study of Electrochemical Preparation of Ferrate(VI) Using Alternating Current Superimposed on the Direct Current Frequency Dependence of Current Yields". Electrochimica Acta, vol. 38, No. 13, 1993, pp. 1717-1720.

(Continued)

Primary Examiner — James D Anderson
Assistant Examiner — William Lee
(74) Attorney, Agent, or Firm — Yimei C. Hammond; Kremblas & Foster

(57) ABSTRACT

Compositions containing ferrate(VI) are disclosed. Also, methods are disclosed that utilize ferrate(VI).

6 Claims, 1 Drawing Sheet

(56) References Cited

U.S. PATENT DOCUMENTS

| | | |
|---|---|---|
| 2005/0022810 A1 | 2/2005 | Moore et al. |
| 2005/0049157 A1 | 3/2005 | MacDonald et al. |
| 2005/0053543 A1 | 3/2005 | Kneip et al. |
| 2005/0123743 A1 | 6/2005 | Martinazzo |
| 2005/0152828 A1 | 7/2005 | Aga et al. |
| 2006/0134339 A1 | 6/2006 | Wang et al. |
| 2006/0162613 A1 | 7/2006 | Rosenhahn et al. |
| 2006/0171907 A1* | 8/2006 | Scott et al. ............... 424/53 |
| 2008/0305341 A1 | 12/2008 | Plieth et al. |
| 2009/0216060 A1 | 8/2009 | Monzyk et al. |
| 2011/0017209 A1 | 1/2011 | Monzyk et al. |

FOREIGN PATENT DOCUMENTS

| | | |
|---|---|---|
| EP | 166825 | 1/2002 |
| FR | 2805162 | 8/2001 |
| JP | 59139314 | 8/1984 |
| JP | 61053398 | 3/1986 |
| JP | 62007596 | 1/1987 |
| JP | 62091225 | 4/1987 |
| JP | 62292492 | 12/1987 |
| WO | 0121856 | 3/2001 |
| WO | 0182896 | 11/2001 |
| WO | 2005069892 | 8/2005 |
| WO | 2006015756 | 2/2006 |
| WO | 2007075153 | 7/2007 |
| WO | 2008112657 | 9/2008 |
| WO | 2009142823 | 11/2009 |
| WO | 2010045657 | 4/2010 |

OTHER PUBLICATIONS

Bouzek, K., Flower, L., Rousar, I., Wragg, A.A.: "Electrochemical Production of Ferrate(VI) Using Sinusoidal Alternating Current Superimposed on Direct Current. Pure Iron Electrode". Journal of Applied Electrochemistry, vol. 29, 1999, pp. 569-576.

Bouzek, K., et al. "Influence of Anode Material on Current Yields During Ferrate(VI) Production by Anodic Iron Dissolution Part I: Current Efficiency During Anodic Dissolution of Grey Cast Iron to Ferrate(VI) in Concentrated Alkali Hydroxide Solutions". Journal of Applied Electrochemistry, vol. 26, 1996, pp. 919-923.

Dean, John A. "Lange's Handbook of Chemistry". 15th edition, 1999, McGraw-Hill, New York, 8.104-8.111.

Delaude et al.: "A Novel Oxidizing Reagent Based on Potassium Ferrate(VI)". Journal of Organic Chemistry, vol. 61, 1996, pp. 6360-6370.

Grube, Von G., Gmelin, H.: "Effects of Superimposed Alternating Current on Anode Ferrate Formation". Zeitschrift fur Electrochemie, vol. 26, 1920, pp. 153-161.

He, W., Wang, J., Yang, C., and Zhang, J.: "The Rapid Electrochemical Preparation of Dissolved Ferrate(VI): Effects of Various Operating Parameters". Electrochimica Acta, vol. 51, 2006, pp. 1067-1973.

Hirota, N.: "Anticorrosion Paints". May 12, 1984, XP002569967, database accession No. 1972:476784.

Hives, J., Benova, M., Bouzek, K., Sitek, J., Sharma, V.K.: "The Cyclic Voltammetric Study of Ferrate(VI) Formation in a Molten Na/K hydroxide Mixture". Electrochimica Acta, vol. 54, 2008, pp. 203-208.

Kim, K.S., Chang, Y., Bae, S.K. and Hahn, C.S.: "Selective Oxidation of Allylic and Benzylic Alcohols Using Potassium Ferrate under Phase-Transfer Catalysis Condition". Synthesis, vol. 10, Oct. 1984, pp. 866-868. XP002438865.

Licht, Stuart, Naschitz, Vera, Wang, Baohui: "Rapid Chemical Synthesis of the Barium Ferrate Super-Iron Fe (VI) Compound, BaFeO4". Journal of Power Sources [Online] vol. 109, Jun. 15, 2002, pp. 67-70, XP002569968 DOI: doi:10.1016/S0378-7753 (02)00041-1 [retrieved on Feb. 23, 2010].

Macova, Z., Bouzek, K, Hives, J., Sharma, V.K., Terryn, R.J., Baum, J.C.: "Research Progress in the Electrochemical Synthesis of Ferrate(VI)". Electrochimica Acta, vol. 54, 2009, pp. 2673-2683.

Sharma, Virender K., "Potassium Ferrate(VI): An Environmentally Friendly Oxidant". Advances in Environmental Research 6 (2002) 143-156.

Yang, W., Zhou, Y., Wang, H. and Bi, D: "Studies on Influence of Various Experimental Conditions on Electrochemical Generation of Ferrate(VI) in NaOH-KOH mixed Electrolyte". Russian Journal of Electrochemistry, vol. 45, No. 7, 2009, pp. 795-799.

First Report mailed May 29, 2009, from Australian Intellectual Property Office, in an Australian patent No. 2005206927.

Notice of Allowance mailed Jun. 4, 2010, from Australian Intellectual Property Office, in an Australian patent No. 2005206927.

The First Office Action fromn The State Intellectual Property Office of The People's Republic of China mailed on Mar. 10, 2010, in the Chinese patent application No. 20050002471.5.

The Second Office Action from The State Intellectual Property Office of The People's Republic of China mailed on Nov. 4, 2010, in the Chinese patent application No. 200580002471.5.

First Office action mailed on Sep. 10, 2010, in a co-pending US patent application publication No. 20090216060 published on Aug. 27, 2009.

Second Office action mailed on Jan. 12, 2011, in a co-pending US patent application publication No. 20090216060 published on AUg. 27, 2009.

Communication from the European Patent Office mailed on Apr. 11, 2008, in a co-pending European Patent Application No. 05858701.5-1218.

Communication from the European Patent Office mailed on Jun. 18, 2010, in a co-pending European Patent Application No. 05858701.5-1218.

Issuance Notice mailed on Nov. 16, 2010, in a co-pending European Patent Application No. 05858701.5-1218.

Written Opinion of the International Searching Authority for International Application Publication No. WO2007/075153 (Application No. PCT/US2005/04714), published on Jul. 5, 2007, Authorized Officer Dalkafouki, A.

International Search Report for International Application Publication No. WO2007/075153 (Application No. PCT/US2005/04714), published on Jul. 5, 2007, Authorized Officer Dalkafouki, A.

Written Opinion of the International Searching Authority for International Application Publication No. WO2008/112657 (Application No. PCT/US2008/056446), published on Sep. 18, 2008, Authorized Officer Pelli Wablat, B.

Written Opinion of the International Searching Authority for International Application Publication No. WO2010/045657 (Application No. PCT/US2009/061204), published on Apr. 22, 2010, Authorized Officer Schmitt, J.

Written Opinion of the International Searching Authority for International Application Publication No. WO2009/142823 (Application No. PCT/US2009/038472), published on Nov. 26, 2009, Authorized Officer Simin Baharlou.

Written Opinion of the International Searching Authority for International Application Publication No. WO2005/069892 (Application No. PCT/US2005/001402), published on Aug. 4, 2005, Authorized Officer Roy King.

* cited by examiner

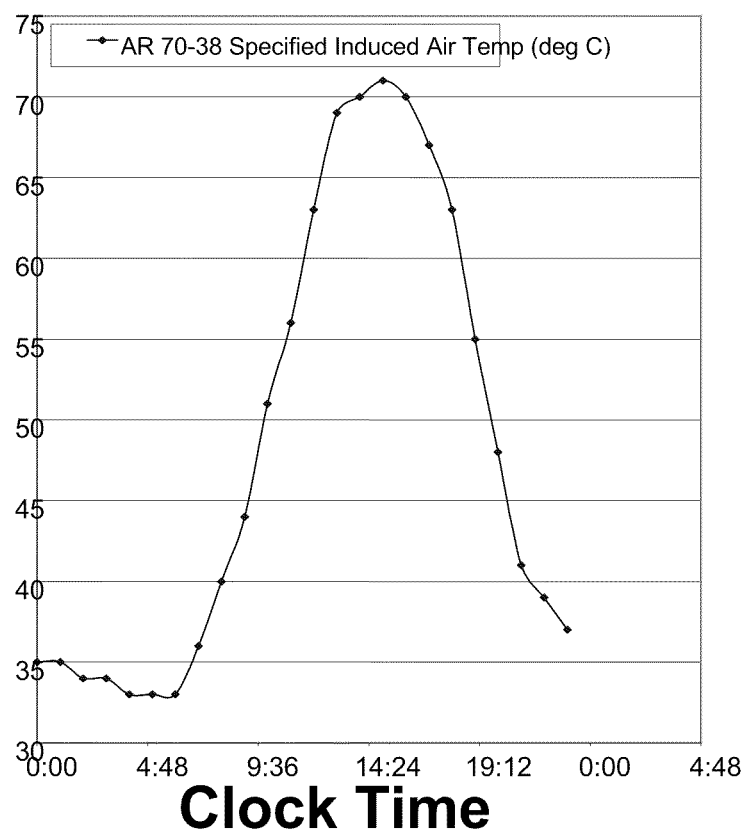

FERRATE(VI)-CONTAINING COMPOSITIONS AND METHODS OF USING FERRATE(VI)

RELATED APPLICATIONS

This application claims the benefit of the priority International Application No. PCT/US2008/056446 filed 10 Mar. 2008, and, by way of the PCT application, of U.S. provisional applications Ser. Nos. 60/893,929, 60/946,134, and 60/946,940 filed 9 Mar. 2007, 25 Jun. 2007 and 28 Jun. 2007, respectively.

BACKGROUND

Ferrate(VI), or "ferrate", has long been known as a powerful oxidant that has found uses in waste water treatment and in batteries. The literature also contains reports of the use of ferrate in certain organic oxidations, surface treatments, and blood clotting.

There are several ways of synthesizing ferrate. One such method is described by Johnson in U.S. Pat. No. 5,746,994 in which $Fe^{3+}$ is oxidized with monoperoxide. Johnson reports that the isolation of potassium ferrate(VI) $K_2FeO_4$ in a sulfate matrix $K_2SO_4$ stabilizes the ferrate against decomposition and inhibits clumping from moisture adsorption. Johnson also mentions that potassium ferrate made by hypochlorite oxidation in strongly alkaline solution and precipitated by the addition of KOH is stable indefinitely when kept dry.

An apparatus for synthesizing ferrate is described in U.S. Published Patent Application No. 2005/0042155 A1.

Ferrate has been proposed for use commercially for water purification and its use in treating waste water has been discussed in scores of publications. For example, Deininger et al. in U.S. Pat. Nos. 4,983,306 and 5,380,443 has described treating water to remove metal ion contaminants, especially the transuranic elements. In this method, the pH of the water is adjusted to about 6.5 to about 14. Ferrate is especially useful for waste water treatment since it can remove a broad range of contaminants, disinfects many types of pathogens, and the iron(III) products coagulate and fall from solution, thereby also clarifying the water.

The use of ferrate in the presence of a phase transfer catalyst has been reported in oxidations of certain organic compounds. Song et al., in Huaxue Tongbao 69(3), 220-223 (2006) reported the conversion of benzyl alcohol to benzaldehyde by reaction with potassium ferrate in the cyclohexane/water in the presence of benzyltrimethylammonium chloride. Similar chemistry was described by Kim et al. in Synthesis, 10, 866-8 (1984).

Patterson in U.S. Pat. No. 6,521,265 described a method of clotting blood by topically applying a ferrate paste to a wound. In this method, the compound is stored dry and unmixed and is mixed into a paste with the patient's blood or other aqueous media just prior to its application to a wound. Patterson states that the oxygen produced during the reaction substantially reduces the level of bacteria, virus and fungus at the wound. After treatment, the wound remains open unless the ferrate salt is combined with a bandage that has been impregnated or coated with a dry powder of one of the ferrate salt compositions.

Metal surfaces can be oxidized with a ferrate solution to form an oxide layer. Minevski et al. in U.S. Pat. No. 7,045,024 describe a process in which an aluminum surface is cleaned and then treated with a ferrate solution for a time ranging from about 1 second to about 5 minutes.

Champi et al. in U.S. Pat. No. 6,974,562 and U.S. Published Patent Application No. 2005/0271575 A1 describe methods of making ferrate immediately prior to use. This is advantageous since ferrate can degrade quickly in the presence of moisture. Champi et al. suggest that the ferrate could be encapsulated for future use in a membrane of molecular sieves, clay, porcelain, or other porous material that is not susceptible to oxidation. The membrane could be slightly water soluble so that the ferrate could be released over time. Champi et al. propose numerous uses for the ferrate, including: as an oxidant to prepare polymer and metal surfaces; removal of color from industrial electrolytic baths, synthesis of Fischer-Tropsch catalysts, purifying hemicellulose, as a selective oxidant in organic chemistry, disinfection as a biocide or virocide, phosphorylase inactivator, paint additive, denitration of flue gas, electrode, detoxifying cyanide from waste water, in cigarette filters, as an oxidant of pulp waste, removal of hydrogen sulfide, purifying waste water and drinking water, as an additive to cement as a structural hardener; as a disinfectant, removal of slime films such as in power plants and shipboard cooling systems, delignification of agricultural residues, magnetic filler for plastics, as a catalyst in burning coal, as a component of grinding wheels, in ceramic encapsulated rare earth ferrates where ferromagnetic properties are needed, removal of textile dyes from wastewater, treatment of boiler chemical cleaning wastes, oxidizing sulfur and cyanide containing compounds generated by oil refineries and coke processing plants, removing Mn from drinking water, removing As from drinking water, destroying chemical warfare agents, removing organic matter from drinking water, purifying water in a Jacuzzi or swimming pool and filtering away the resulting iron salts, cleaning waste water from animal and vegetable processing, treatment of any aqueous stream containing biosolids, radioactive cleanup, oxidizing pretreatment of chromium containing films, removing heavy metals from solution, cleaning or disinfecting metallic surfaces in medical devices or in the semi-conductor industry, disinfecting and cleaning instruments and surfaces for medical uses, and cleaning bilge water from ships.

SUMMARY OF THE INVENTION

In this invention, ferrate(VI) can have several actions. One such action is stain removal; for example, removing stains caused by food, tobacco, grass stains, or oil. Another action is odor removal; examples include removing pet smells, removing skunk smell, as an air freshener, and in an air filter. A third action is as a disinfectant—killing bacteria, viruses, mold, mildew, protozoa, other microorganisms, and also head lice or insects. Another action is destruction, for example in disposing of unwanted drugs, toxic industrial compounds, toxic pesticides, or herbicides.

The actions of ferrate(VI) can be applied in several ways. One application is oral care; for example using powders, pellets, pills, lozenges tablets, creams, salves, ointments, and the like, for killing mouth bacteria or viruses, removing mouth odor, or removing tooth stains and disinfecting tooth caries, e.g. by rinsing, brushing, and the like. Another application is in personal care; for example, bleaching hair, lightening tattoos, lightening skin color (for example scar tissue) or mole removal. Another application is applying tablets, briquettes, or powder as packets of ferrate(VI) for water purification, or for cleaning camping utensils. Another area for application is in home care; examples include drain clearing, or cleaning walls, floors, counters, clothing, or carpets.

In one aspect, the invention provides a composition comprising: ferrate(VI) and a hydrophobic material encapsulating the ferrate, wherein the hydrophobic material is soluble in organic solvents or soaps or detergents in the presence of moisture.

In another aspect, the invention provides a method of cleaning an article, comprising: providing a formulation comprising ferrate(VI); and applying the formulation comprising ferrate(VI) to a surface of the article. In this aspect, the article comprises fabric, carpet, furniture, flooring, wall covering, sinks, basins, toilets or other plumbing appliances. In one preferred embodiment, the article comprises clothing and the clothing having the formulation applied to it is washed in a washing machine.

In another aspect, the invention provides a composition comprising ferrate and a food. In one method, this composition can be used to kill insects by placing the composition in an area visited by insects.

In a further aspect, the invention provides a composition comprising: ferrate and a medicant or a component to assist in transporting ferrate across a cell wall or protein coat. In a preferred embodiment, the composition further comprises a pH modifier.

In another aspect, the invention provides a method of treating a human or nonhuman animal, comprising: administering ferrate into a body; wherein the step of administering is subcutaneous or oral. For example, ferrate can be administered to neutralize a poison within the body.

In a further aspect, the invention comprises article comprising: a ferrate composition comprising at least 1% by weight ferrate, and a container with a pressure release valve. The ferrate composition is inside the container. The container could be a can or other suitable container.

In another aspect, the invention provides a method of treating fur or hair, comprising: providing a ferrate composition, and applying the ferrate composition to the fur, skin or hair. For example, the ferrate(VI) composition could be applied to an animal that has been sprayed by a skunk. In a bleaching application, the ferrate(VI) composition is left on the hair, skin or fur for a sufficient time to decrease the color of the hair or fur. In a disinfecting application, a ferrate(VI) composition is left on the hair, skin or fur for a sufficient time to kill at least 10% of organisms that are on the fur, skin or hair.

In another aspect, the invention provides a method of treating an infected plant, comprising: providing a ferrate composition, and applying an effective amount of the ferrate composition onto the plant. In a preferred embodiment, the method reduces the amount of infective agent by at least 10%.

In another aspect, the invention provides a method of cleaning a toilet, comprising: adding a ferrate composition to a toilet bowl; and flushing the toilet. In a preferred embodiment, the ferrate composition is added as a solid to the toilet. In another preferred embodiment, the ferrate composition comprises an abrasive. In some embodiments, the ferrate composition consists essentially of pure ferrate.

In a further aspect, the invention provides a method of declogging a drain, comprising: providing a ferrate composition, and adding the ferrate composition to water in a clogged drain. In a preferred embodiment, the composition comprises 40-52 weight % NaOH or KOH, 0.1 to 58 weight % sodium or potassium ferrate(VI), and 0 to 60 weight % water. In another preferred embodiment, the ferrate(VI) in the composition comprises ferrate(VI) crystals having an aspect ratio of at least 10.

In another aspect, the invention provides a method of cleaning a mouth, comprising: providing a ferrate(VI) composition, and applying the ferrate(VI) composition to the inside of the mouth. Similarly, the invention provides a method of bleaching teeth, comprising: providing a formulation comprising ferrate(VI); and applying an effective amount of the formulation comprising ferrate(VI) to the surface of a tooth.

In another aspect, the invention provides a toothpaste, comprising: ferrate, and at least one ingredient selected from: an abrasive, a desensitizing agent, fluoride, a chelating agent, tetrasodium pyrophosphate, sodium tripolyphosphate, xylitol, a humectant, and a thickener. Toothpaste ingredients usable in the present invention, in addition to ferrate, include any of the ingredients known in the art. Examples include: fluoride (typically sodium fluoride or sodium monofluorophosphate), antibacterial agents (such as Triclosan or zinc salt), sodium bicarbonate, enzymes, xylitol, abrasives (such as hydrated silica, dicalcium phosphate digydrate, calcium carbonate, sodium bicarbonate, calcium pyrophosphate, alumina), surfactants (such as sodium lauryl sulfate, sodium N-lauryl sarcosinate, sodium lauryl sulfoacetate) humectants (such as glycerine, polyethylene glycol, polypropylene glycol, sorbitol), thickeners (such as carrageenan, clays, sodium aluminum silicates, gums), preservatives (such as sodium benzoate), desensitizing agents (such as strontium chloride, potassium nitrate, potassium citrate) flavorings (aspartame, sucralose, xylitol, sorbitol, mannitol, etc.), buffers, and coloring agents. The invention also includes methods of cleaning the mouth (especially teeth) using a ferrate(VI) composition.

The invention also provides a chewing gum that comprises ferrate along with an elastomer. Preferably, the ferrate(VI) is encapsulated to enhance stability, and/or the gum can be packaged in a package having little or no permeability to air or moisture. Chewing gums of the invention may include any of ingredients known in the chewing gum arts, including: natural elastomers such as chicle or other latexes, food grade synthetic elastomers, plasticizers, softeners such as vegetable oil, wax, flavorings, natural or artificial sweeteners (aspartame, sucralose, xylitol, sorbitol, mannitol, etc.). One preferred gum formulation uses ferrate(VI) encapsulated in particles and having the particles dispersed in a gum matrix. The invention also includes methods of cleaning the mouth (especially teeth) by chewing ferrate-containing gum. Chewing gum containing a percarbonate whitener is disclosed in U.S. Pat. No. 5,824,291, which is incorporated herein by reference and includes descriptions of gum ingredients.

In a further aspect, the invention provides a method of disposing of unwanted drugs, comprising: providing a ferrate composition, and combining the ferrate composition with an unwanted drug.

In another aspect, the invention provides a method of washing food, comprising: providing a ferrate composition, and applying the ferrate composition to a food. Preferably, the food comprises a fruit or vegetable.

In another aspect, the invention provides a cleaning formulation, comprising:
a matrix material; and an effective amount of ferrate(VI) dispersed in the matrix material;
wherein the matrix material comprises any of the components discussed herein. In some embodiments, the cleaning formulation comprises a solid solution of ferrate(VI) ion with potassium sulfate, calcium sulfate, magnesium sulfate, sodium sulfate, and zinc sulfate, or combinations of these. In some embodiments, the cleaning formulation comprises a solid solution of ferrate(VI) ion with a carrier salt wherein the carrier salt is doped with ferrate(VI) ions to the weight fraction from $10^{-5}$ to 10% of the formulation or from 0.05 to 0.5% of the formulation. In some preferred embodiments, the ferrate(VI) ion is disposed in an aqueous gel. In some embodiments, the ferrate(VI) ion is disposed in a hydrocarbon or silicone composition, which may be a grease or solid comprising these materials. In some embodiments, the cleaning formulation comprises a flavoring agent. In some embodiments, the cleaning formulation comprises an edible polyhydric alcohol. The cleaning formulation may be "self-indicating" in that the color of the ferrate(VI) indicates it is present and active and a change in color indicates it has reacted.

In another aspect, the invention provides a formulation and/or method of cleaning a surface comprising a material that is "self-indicating" in that the color of the formulation indicates it is active and a change in color indicates it has reacted.

In a further aspect, the invention provides a method of cleaning a surface, comprising: providing a ferrate(VI) composition that comprises ferrate and a phase transfer catalyst or a chelating agent, and applying the ferrate(VI) composition to the surface. For example, the surface may be a surface of a wall, counter, floor, toilet, sink, carpet. In some embodiments, an aqueous composition comprising a pH modifier is first applied to the surface, and then ferrate is dissolved into the aqueous composition. In some embodiments, the pH modifier comprises dipotassium hydrogen phosphate.

In another aspect, the invention provides a method of cleaning clothing, comprising: providing a ferrate composition that comprises ferrate and a phase transfer catalyst or a chelating agent, and applying the ferrate composition to the clothing.

In yet another aspect, the invention provides a cleaning composition, comprising, ferrate, and at least one of the following groups: a) a chelating agent; b) a phase transfer catalyst and a phosphate; or c) an abrasive. In a preferred embodiment, the ferrate(VI) in the composition comprises crystals having an aspect ratio of at least 10.

In another aspect, the invention provides a dispenser for ferrate, comprising: a first compartment comprising dry ferrate; and a second compartment comprising water or an aqueous solution.

Any of the additives described herein can be used in ferrate formulations, and, in the broadest aspects of the invention, any of the formulations can be used in any of the inventive methods. For example, the invention provides cleaning formulation, comprising: a matrix material; and an effective amount of ferrate dispersed in the matrix material; wherein the matrix material comprises any of the components discussed herein.

In this the description of this invention, "providing" includes obtaining a pre-made ferrate-containing composition, or mixing two or more components to make a ferrate-containing composition. "Applying" means that a composition is applied to an article either before, after or during the formation of a ferrate. The term "comprising" is an open term that means "including," and any of the inventive aspects that are described as "comprising," may, in alternative embodiments be described using the narrower terms "consisting essentially of" or "consisting of." All "%" indicates weight % unless indicated otherwise.

BRIEF DESCRIPTION OF THE FIGURE

FIG. 1 shows the AR 70-38 Hot-Dry Temperature Cycle Requirement as described in Example 1.

DESCRIPTION OF THE INVENTION

Ferrate(VI), or just "ferrate" is non-persistent with respect to being hazardous, toxic, or having adverse environmental impact regardless of most use conditions. It is capable of desirable bleaching chemistry, and is storage and temperature stable. It is also purple in color, even when formulated, and it changes to orange when in spent form (chemically reduced to harmless and stable ferric compounds). To many consumers and those skilled in the art of staining it will be surprising that a colored composition, especially one containing iron, can be a whitener or a stain remover, and not leave a iron stain itself. It is a useful feature of the ferrate(VI) formulation of the invention that the products do not leave a "red rust" stain.

Ferrate(VI) is sometimes termed herein as simply "ferrate." Hence "ferrate" is used in this specification to represent ferrate(VI), and the use of oxidation state Roman numerals is also sometimes used to insure unambiguous naming of compounds. As used herein, "ferrate" does not refer to just any compound that contains iron; for example hexacyanoferrate (II) is not "ferrate" in the descriptions herein.

The amount of ferrate(VI) used in a formulation of the invention can vary depending on the intended application. In some embodiments, ferrate(VI) (measured as weight % iron) is present in an at least about 0.00001% by weight of the formulation, in some embodiments, 10% or less, preferably from about 0.001% to about 20%, and more preferably from about 0.05% to about 10%. In some embodiments, a composition contains at least 40%, or at least 50%, or at least 70%, or at least 90%, and in some embodiments is essentially pure ferrate, normally 90-99+%.

The concentration of ferrate(VI) in a sample can be determined by UV/vis spectrophotometry by comparing the concentrations of ferrate(VI) determined by dissolving in an aqueous solution of 32% NaOH and measuring the absorbance readings at 505 and 785 nm. For the measurement to be qualitatively and quantitatively correct, the concentrations derived from each absorbance reading should be the same within 2-10%. If these two values differ more than 10%, and the spectrum is consistent with ferrate(VI) ion being the lone chromophore and that another colored material is also present. Also, the presence of colloids or particulates is indicated that scatter light causing a false high in the concentration measurement. In this event, further purification of the analytical sample is required, by centrifugation or filtration, to remove these particulates and/or colloids and the absorbance is then re-read at the two diagnostic wavelengths. In addition, for accurate measurement, care should be taken to avoid conditions that would change the oxidation state of iron. The NaOH solution should be free of reducing agents. If necessary, where a ferrate(VI) containing composition is strongly hydrophobic, the hydrophobic matrix may be removed (such as with toluene or phase transfer catalyst, i.e. quaternary ammonium ion, a blend of quaternary ammonium ions, phosphonium ion, a blend of phosphonium ions), for example by water washing the ferrate(VI) ion from the hydrophobic phase, just prior to dissolving the ferrate(VI) in 32% NaOH.

Unexpectedly, unlike all peroxide materials, we found that potassium ferrate(VI) to be thermally stable as defined by Army Regulation (AR) 70-38 test conditions. Therefore potassium ferrate(VI) was determined to be stable to storage for long periods, at least 98 days at 71° C., and at least 82 days under conditions of cycling daily from 23° C. to 71° C. and back again. This result is true regardless of whether the potassium ferrate(VI) is pure (80-100% analytical grade) or of only moderate purity (50-80% technical grade). In these tests, losses with time varied slightly with test vials ranging from <1% to 10% (±3%) loss respectively after the test periods given. From these results, it can be estimated that the potassium ferrate(VI) will likely be sufficiently stable for several years of storage, at least.

An additional feature of using ferrate(VI) is the enhanced scrubbing and agitation that can be provided when formulations are used that cause at least a portion, preferably a small portion (<10%), and most preferably a very small portion (<2%), of the ferrate(VI) contained therein to oxidize water to $O_2$ gas which then forms fine bubbles. Such fine bubbles are known in the art of surface finishing to efficiently stir fluids in bulk and especially adjacent to surfaces, that is microscopically agitate, or mix chemicals at surfaces being cleaned and/or otherwise treated, i.e. the bleaching of stains on teeth surfaces.

Despite the strong oxidation potential of ferrate(VI), some useful ferrate(VI) compositions can be made with an oxidation resistant or nonoxidizable matrix materials selected from one or a combination of the following materials: water, water-polymer, water-oil emulsions, water-hydrocarbon, oil only, hydrocarbons only, silicones, alkaline or neutral silicates, silicas including meta silicates, phosphates, phosphate esters, meta phosphates, polyphosphates, borates, boric acid esters, fluborates, and the like, alone or in combination, and/or with a matrix material in which at least one salt of ferrate(VI) is not or poorly soluble, for example with aliphatic and/or aromatic hydrocarbons such as waxes, petroleum, petroleum jellies, or synthetic oils, creams, ointments, solids, solvents, greases, heat transfer fluids, solvent cleaners, paint thinners, petroleum and/or biodiesel fuels, petroleum jellies, gels, agricultural pesticide diluents, hydraulic fluids, and the like, alone or in any combination. A particularly preferred formulation is a combination of ferrate(VI) salt, most preferably the potassium salt and/or sodium salt, with one or more nonoxidizable material(s) and/or one or more matrix materials in which at least one salt of ferrate(VI), most preferably potassium and/or sodium ferrate(VI), is not soluble. For example, nonoxidizable materials include toluene, benzene, petroleum jelly, and the like.

Hydrophobic materials that are resistant to reaction with ferrate(VI) are desirable matrix materials for some applications. Examples include polyolefins such as polyethylene, polypropylene, polyethers, polyesters, salts of polycarboxylic acids, and the like, alone or in combination as co-polymers or physically blended. The hydrophobic material listed above could be removed, such as by exposure to an organic solvent, by evaporation, by breaking/grinding, or by environmental degradation, prior to use of the ferrate.

In its broader aspects, the invention is not limited to a specific form of ferrate(VI). The chemical form of the ferrate (VI) can be varied, and may be, for example, an essentially pure water soluble salt, an essentially partially water soluble salt, an essentially insoluble water soluble salt, as solid solutions with ions such as with sulfate, fluoride, phosphate, silicate, carbonate, polyphosphate, pyrophosphate, tripolyphosphate, and the like. Such salts of ferrate(VI) can contain counter ions (cations) of K, Na, Rb, Cs, Ca, Mg, Zn, Al, Li, La, Ba, Ga, lanthanides, Sc, Y, quaternary ammonium ion, a blend of quaternary ammonium ions, phosphonium ion, a blend of phosphonium ions, 1-hexadecylpyridinium ion, N-methyl trialkylammonium ion, N-methyl trialkylbenzene ammonium ion, alone or as solutions and/or mixtures. Of this list, for aqueous or hydrophilic applications, K, Na, Ca, Mg, Zn, and Al are preferred, while K is most preferred. For non-aqueous or hydrophobic applications, inclusion of a quaternary ammonium ion into the operation or product formulation is preferred. Other components of a suitable formulation may include (but are not limited to) oxidation-resistant phase transfer catalysts, surfactants, pH buffers, and/or iron-chelating agents.

Phase transfer catalysts, preferably quaternary ammonium or phosphonium salts, preferably N-methyl-tri-N-alkyl with linear or branched alkyl chains preferably from C6 to C18, most preferably C8 to C12, can be present from 0% to 50% of the amount of ferrate, in some embodiments from about 5% to 20%.

Surfactants may be any oxidation-resistant anionic, cationic, and non-ionic surfactants. Suitable anion surfactants include carboxylates, sulfonates, sulfates, and phosphates and orthophosphate ester containing hydrophobic chains including linear or branched alkyl, alkylarene chains, with carbon numbers from C8 to C18, preferably C12 to C16, or mixtures thereof, or petroleum sulfonates. Suitable nonionic surfactants include mono- and diethanol amines, alkyl- and alkylarylethoxylates, or mixtures thereof, containing hydrophobic chains including linear or branched alkyl, alkylarene chains, and the like with carbon numbers from C8 to C18, preferably C12 to C16, Suitable cationic surfactants include amines or quaternary ammonium surfactants, and the like, or mixtures thereof, containing hydrophobic chains including linear or branched alkyl, alkylaryl chains, with carbon numbers from C8 to C18, preferably C12 to C16. If used, surfactants can be present, in some preferred embodiments, from 0.01% to 300%, based on ferrate.

Buffers to regulate the pH of the composition and solutions resulting from use of the compositions can include any oxidation resistant buffer system with a pH of 6 to 12, preferably 7 to 8. Examples include mono- and di-basic phosphates, phosphonic acids, sulfonates, amines, and the like, including multifunctional di- and tri-phosphates, diamines, and the like, and mixtures thereof. The multifunctional buffer systems may also act as iron-chelating agents. Different buffering systems may be used at different times during a reaction sequence to optimize acid-base conditions. Suitable compositions contain sufficient buffering capacity to control the pH during reaction of the composition with a substrate.

Iron-chelating agents include suitable oxidation resistant di- or tri-functional molecules with the ability to form 5 or preferably 6-membered rings upon chelation. Examples include bi- and tri-dentate bis- or tris-phosphonic acids, bis- and tris-amines, their salts, and mixtures thereof, and hydroxamic acids, including N-methyl acetyl- and N-methyl benzyl hyroxamic acid and the like or mixtures thereof. Preferred compositions include from 300 to 5000 percent of iron-chelating agent based on ferrate, more preferably from 500 to 1000 percent.

In many applications, acids with apparent or actual pKa values less than 6, and preferably less than 7, and more preferably less than 8, readily oxidized alcohols, amines, aldehydes, thiols and phenolics typically should be avoided unless these compounds or functional groups are first rendered oxidation resistant by neutralization, derivatization or thorough removal of moisture. Such incompatible materials could be co-formulated with a ferrate(VI) formulation in some instances where two or more part formulations are desirable. These incompatible combinations can be valuable in some instances due to synergistic effects. For example, two part formulations between ferrate(VI) as "Part A" and acidic "Part B" materials where acidic "B" materials (or materials that can be rendered acidic by co-addition of an acid) can be as one or more parts consisting of a combination of one or more of the following materials:

One or more carboxylic acids and/or their salts [i.e. one or more of the following in any combination and which normally would consist of at least one —COOH and/or —COO⁻ group bonded to atoms of C and H as "hydrocarbons" of aliphatic or aromatic groups, or a combination of aromatic and aliphatic groups ("alkyl aryl"), of carbon number range of 1 to about 40 when present as individual compounds, or with a molecular weight of 200 to about 10,000 Daltons when present as oligomers, or with a molecular weight of 2,000 to about 3,000,000 Daltons when present as polymers, and which can also contain groups or atoms of non-C and H such as halogens, pseudo halogens, oxygen (including ethers, alcohols, carboxylic acids, ketones, aldehydes, and the like), nitrogen (including one or more nitro groups, nitroso groups, nitriles, amides, imines, amines, zwitterions, betaine groups, and the like], such as
- as a monocarboxylic acid and/or their salts selected from acetic acid, propionic acid, benzoic acid, salicylic acid, formic acid, butyric, valeric, caproic, caprylic, capric, lauric, myristic, palmitic, stearic, oleic, linoleic, cyclohexanecarboxylic, phenylacetic, toluic (o, m and/or p), chlorobenzoic (o, m and/or p), bromobenzoic (o, m, and/or p), nitrobenzoic (o, m and/or p), phthalic, isophthalic, terephthalic, p-hydroxybenzoic, anthranilic, aminobenzoic acid (o, m and/or p), methoxybenzoic (o, m and/or p), and the like;
- and/or dicarboxylic acids and/or their salts selected from succinic acid, malonic acid, oxalic acid, glutaric, adipic, pimelic, suberic, azelaic, sebacic, maleic, fumaric, phthalic, isophthalic, terephthalic, hemimellitic, trimellitic, trimesic, and the like;
- and/or tricarboxylic acids selected from citric acid, and the like;
- And/or polycarboxylic acids and/or their salts selected from polyacrylic acid, polysulfonic acid, polymethacrylic acid, copolymers, block copolymers, and the like.
and/or sulfonic and other sulfur-based acid selected from methanesulfonic acid, petroleum sulfonates, sulfuric acid, lauryl sulfonic acid, toluenesulfonic acid (o, m and/or p), organosulfonic acid, singular or polysulfonated aromatic compounds, alkylsulfonic acid, arylsulfonic acid, alkylarylsulfonic acid, and the like.
- And/or polysulfonic acid and/or their salts including copolymers, block copolymers, containing hydroxyl groups, or keto groups, and the like as listed above.
and/or acidic inorganic salts such as sodium and potassium salts of hydrogen sulfate,
and/or protonated phosphates such as phosphoric acid, orthophosphate (monobasic), protonated phosphonates and phosphinics,
and/or silica gel, aerogel, fumed silica, diatomaceous earth, and the like, and most preferably pre-washed with an acetic aqueous solution or other acidic material.
And/or alumina, preferably fine grained alumina, and most preferably alumina pre-washed with an acetic aqueous solution or other acidic material.
and/or bicarbonate ion, $HCO_3^-$, and its salts, and carbonate ion, $CO_3^=$; and its salts,
and/or boric acid,
acidic metal ion salts such as cationic ions of aluminum, zinc, ferric ion, ferrous ion, magnesium ion, lithium ion, titanium(III or IV), gallium, stannic ion, a rare earth group ion, and the like;
HF and HF-releasing reagents,
Mineral acids such as HX where X=halogen and/or pseudo halogen, sulfuric acid, trifluoroacidic acid, phosphoric acid, and the like.

Such pH and ferrate(VI) reactivity control reagents are useful to blend with ferrate at the point of its use to provide any one or a combination of controlling the ferrate(VI) oxidation reaction, preventing high pH values in the reaction product mixture, rendering the ferric product lightly or non-colored, rendering the ferric product water soluble and/or as a dispersible particulate, coagulating and/or flocculating the ferric product. The rate of this reaction is set using control of the pH where the higher the acid/ferrate(VI) ratio the faster and more aggressive is the reaction of ferrate. Lowering of the acid/ferrate(VI) ratio lowers the ferrate(VI) reaction rate and oxidative aggressiveness. Chloride ion, and other halides and pseudo halogens, increase the reactivity of ferrate(VI) ion causing its oxidation reactions to proceed faster and more aggressively. Reactions, such as bleaching, can be sped up by such means from many tens of minutes to a less than one minute, and even to just a few seconds.

Ferrate can be mixed with other ingredients as mixtures or solid solutions with which it is compatible when used alone or as a Part A in a multiple part system; for example, to provide ease of use and/or to effect faster, more efficient, and/or more complete whitening, bleaching, sterilization, and/or cleaning properties. One preferred formulation includes solid solutions of ferrate(VI) ion by ion substitution to form carrier salt materials, preferably with sulfate ion materials, such as with potassium sulfate, calcium sulfate, magnesium sulfate, sodium sulfate, aluminum sulfate, and zinc sulfate, including the basic (hydroxide ion containing) forms, and/or chromate (VI) forms, of one or a combination of the following minerals,
Jarosite structure, $[KFe_3(SO_4)_2(OH)_6]$,
and/or Kuzelite, $[Ca_4Al_2(SO_4)(OH)_{12}*6H_2O]$,
and/or calcium aluminum chromate hydrate, $[Ca_4Al_2O_6(CrO_4)*(9-14)H_2O]$
and/or calcium aluminum sulfate hydrate, $[Ca_4Al_2O_6(SO_4)*14H_2O]$
and/or Ettringite, $[Ca_6Al_2(SO_4)_3(OH)_{12}*26H_2O]$ Ferrate can be mixed with other ingredients as mixtures or solid solutions. One preferred formulation method includes preparation of solid solutions of ferrate(VI) ion by ion substitution of at least a 1 mol % portion, preferably at least 10 mol % of sulfate ion ($SO_4^=$) and/or chromate ion ($CrO_4^=$) to form carrier salt materials of ferrate ion ($FeO_4^=$). These are normally produced by the co-crystallization method. Such inorganic materials, salts and minerals include one or any combination of the following:
potassium sulfate (arcanite), calcium sulfate, magnesium sulfate, sodium sulfate, aluminum sulfate, barite (BaSO4), and zinc sulfate,
basic (hydroxide ion containing) forms of the above, and/or chromate(VI) replacement forms,
any of the following minerals,
Aluminite, (Al2(SO4)(OH)4*7H2O
Alunogen, (Al2(SO4)3*18H2O
Anhydrite, (CaSO4)
Gypsum, (CaSO4*2H2O)
Bloedite, (Na2Mg(SO4)2*4H2O
Glauberite, $(Na_2Ca(SO_4)_2)$
Hauyne, $((Na,Ca)_{4-8}Al_6(SiO_4)_6(SO_4)_{1-2}$
Kainite, (KMg(SO4)Cl*3H2O
Kieserite, (MgSO4*H2O)
Potassium jarosite, $[KFe_3(SO_4)_2(OH)_6]$,
Kuzelite, $[Ca_4Al_2(SO_4)(OH)_{12}*6H_2O]$,
calcium aluminum chromate hydrate, $[Ca_4Al_2O_6(CrO_4)*(9-14)H_2O]$
calcium aluminum sulfate hydrate, $[Ca_4Al_2O_6(SO_4)*14H_2O]$
Ettringite, $[Ca_6Al_2(SO_4)_3(OH)_{12}*26H_2O]$ Where with each mineral listed above, the $SO_4^=$ is partially or entirely replaced with $FeO_4^=$ ions which have essentially identical molecular dimensions and identical molecular ion electric charge to sulfate ion and chromate ion, and so readily forms solid state "solutions" with minerals and salts of these ions when they are co-crystallized in the same solution. In the above "solid solution" compositions of matter the carrier salt or mineral contains ferrate(VI) ions to the mole fraction of ferrate/sulfate ion or ferrate/chromate ion, is preferably from 1 to 100%, more preferably 2-10%. When substitution is 100% the new ferrate(VI) compositions of matter are:

potassium ferrate(VI) (ferrate version of arcanite), calcium ferrate, magnesium ferrate(VI), sodium ferrate(VI), aluminum ferrate, ferrate version of barite ($BaFeO_4$), and zinc ferrate(VI), basic (hydroxide ion containing) forms of the above, and/or chromate(VI) replacement forms, one or a combination of the following minerals, Ferrate version of aluminite, $[Al_2(FeO_4)(OH)_4*7H_2O]$
Ferrate version of Alunogen, $[Al_2(FeO_4)_3*18H_2O]$
Ferrate version of Anhydrite, $[CaFeO_4]$
Ferrate version of Gypsum, $[CaFeO_4*2H_2O]$
Ferrate version of Bloedite, $[Na_2Mg(FeO_4)_2*4H_2O]$
Ferrate version of Glauberite, $[Na_2Ca(FeO_4)_2]$
Ferrate version of Hauyne, $[(Na,Ca)_{4-8}Al_6(SiO_4)_6(FeO_4)_{1-2}]$
Ferrate version of Kainite, $[KMg(FeO_4)Cl*3H_2O]$
Ferrate version of Kieserite, $[MgFeO_4*H_2O]$
Ferrate version of Potassium jarosite, $[KFe^{III}_3(Fe^{VI}O_4)_2(OH)_6]$,
Ferrate version of Kuzelite, $[Ca_4Al_2(FeO_4)(OH)_{12}*6H_2O]$,
Ferrate version of calcium aluminum chromate hydrate, $[Ca_4Al_2O_6(FeO_4)*(9-14)H_2O]$
Ferrate version of calcium aluminum sulfate hydrate, $[Ca_4Al_2O_6(FeO_4)*14H_2O]$
Ferrate version of Ettringite, $[Ca_6Al_2(FeO_4)_3(OH)_{12}*26H_2O]$ Note that the use of solid solutions dilute the ferrate(VI) ion to enable it to be spread more evenly at low levels, helps control the rate of $O_2$ generation during self mixing for de-staining applications involving porous surfaces, and/or prevents spontaneous premature decomposition by the reaction of two ferrate ions reacting to produce $O_2$ gas.

Other solid solutions of sulfate may include solutions comprising sodium ion, lithium ion, potassium ion, or other alkali metal ions or alkaline earth ions. Especially preferred formulated materials are anhydrous potassium sulfate and/or anhydrous calcium sulfate solid solutions of ferrate(VI) ion. In these above "solid solution" compositions of matter the carrier salt or mineral contains ferrate(VI) ions to the mole fraction of ferrate/sulfate ion, is preferably from 1 to 100%, more preferably 2-10%. As examples, the following is a list of some ferrate(VI) composition mineral-based compositions:

Ferrate(VI) solution of jarosite structure, i.e. $[KFe_3(Fe^{VI}O_4)_2(OH)_6]$ as an essentially pure compound or fraction of potassium jarosite material. This new composition also pertains to other jarosites too, such as where $K^+$ is replaced in whole or in part by $Na^+$, $Ag^I$, $NH_4^+$, $Tl^+$, $Li^+$, and the like, where again Roman numeral subscripts refer to formal oxidation states on the metal ion, while +'s and −'s refer to electric charges on the ions.

Ferrate(VI) solution of Kuzelite, $[Ca_4Al_2(Fe^{VI}O_4)(OH)_{12}*6H_2O]$, as an essentially pure compound or fraction of Kuzelite material.

Ferrate(VI) solution of calcium aluminum chromate hydrate, $[Ca_4Al_2O_6(Fe^{VI}O_4)*(9-14)H_2O]$, as an essentially pure compound or fraction of calcium aluminum chromate hydrate material.

Ferrate(VI) solution of calcium aluminum sulfate hydrate, $[Ca_4Al_2O_6(Fe^{VI}O_4)*14H_2O]$. calcium aluminum ferrate hydrate Ferrate(VI) solution of ettringite, $[Ca_6Al_2(Fe^{VI}O_4)_3(OH)_{12}*26H_2O]$ The above listed materials in completely or substantially dehydrated form.

silicates, clays, oxides, sulfates, and /or phosphates, any combination of those listed above.

In any of the above "solid solution" new compositions of matter the carrier salt or mineral contains ferrate(VI) ions to the mole fraction of ferrate/sulfate ion or ferrate/chromate ion, from $10^{-5}$ to 100%, preferably $10^{-3}$ to 20%, and most preferably 0.05 to 10%.

The Ferrate(VI) compositions of this invention can take many physical forms. Examples include powders, crystals, pastes, gels, granules, pellets, tablets, impregnated pads, lozenges, briquetts, pills, ointments, salves, dusts, Bingham plastics, (i.e., imbedded into oligomers and polymers to form plastics, liquids, caulks, pastes, glues, and the like), creams, foams, and combinations of these. Also effective are materials that change physical form during use—for example a specially formulated emulsions, liquids, gels or creams that changes to foam upon dispensing. Such foaming materials, such as shaving cream, spray insulation, adherent cleaner foam formation technology are already well known in the prior art and are to be considered to be incorporated herein. with the change to incorporate the ferrate-containing materials described above.

Ferrate(VI) can be combined with materials that promote its incorporation into the above-listed materials, including binders, compatibilizers, homogenizers, stabilizers (chemical and physical), and/or diluents.

For applications for human or nonhuman animals, government approved additives can be used in the ferrate(VI) alone or as multi-part compositions. Examples include: gum acacia, Acesulfame Potassium, sugars, sugar alcohols, cyclodextrin, alumina, titania, silica, silicates such as aluminum magnesium silicate, Aluminum Monostearate, aspartame, bentonite, benzaldehyde, Benzalkonium Chloride, Benzethonium Chloride, benzoic alcohol, Benzyl Alcohol, Benzyl Benzoate, beta-carotene, butyl alcohol, Calcium Carbonate, Calcium Phosphate, Calcium Stearate, Calcium Sulfate, vegetable oils, Carbon Black, Carboxymethylcellulose, Carrageenan, cellulose and its derivatives, Cetostearyl Alcohol, hexadecanol, Hexadecanoic acid hexadecyl ester, cetyl esters wax, charcoal, Cholesterol, Cocoa Butter (which is also a type of vegetable oil), Croscarmellose Sodium (a tablet disintegrant), Crospovidone (a tablet disintegrant), Cyclopolydimethylsiloxane, Diacetylated Monoglycerides, Dibutyl 1,8-octanedicarboxylate, Diethanolamine, Diethyl Phthalate, Dimethicone, Docusate Sodium, Ethyl Acetate, Ethylcellulose, Gelatin, Glycerin, Glyceryl Monostearate, Glyceryl Palmitostearate, Glycofurol, Guar Gum, Hydroxyethyl Cellulose, Hydroxypropyl Cellulose, Hydroxypropyl Methylcellulose, Hydroxypropyl Methylcellulose Phthalate, Imidurea, Isopropyl Myristate, Isopropyl Palmitate, Kaolin, Lactitol, Lanolin, Lecithin, ammonium lauryl sulfate, Guar hydroxypropyltrimonium chloride, Menthol, Methyl Cellulose, Methyl Isobutyl Ketone, Methyl Paraben, Mineral Oil, 2-Aminoethanol, Nonoxynol 9, Magnesium Aluminum Silicate, Magnesium Carbonate, Magnesium Oxide, Magnesium Silicate, Stearate, Pectin, petroleum jelly, (Propanoic acid, 2-hydroxy-, homopolymer), Poly(methacrylic acid, methyl methacrylate), Polydextrose, Polyethylene Glycol Monoleyl Ether, Polyethylene Glycol Monostearyl Ether, Polyethylene Oxide, Polymethacrylates, Polyoxyethylene Alkyl Ethers, Polysorbate, Polyvinyl Alcohol, Potassium Benzoate, Povidone, Propyl 3,4,5-trihydroxybenzoate, Propylene Carbonate, Propylene Glycol, alginates, Sodium Benzoate, Sodium Borate, Sodium Citrate, methane sulfonic acid, (which is neutralized in the formulation but provides a useful pH adjustment downwards to offset the pH rise ferrate(VI) can cause in certain cases, e.g. when ferrate(VI) does not have anything else to react with and so reacts with water: i.e.

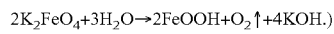

$$2K_2FeO_4 + 3H_2O \rightarrow 2FeOOH + O_2\uparrow + 4KOH.)$$

Sodium Lauryl Sulfate, Sodium thiosulfate (this reagent will instantly reduce ferrate to ferrous/ferric, and so is a way to quickly discharge ferrate(VI) when desired), Sorbitan derivatives, Starch, Stearyl Alcohol, Sulphur Dioxide, Thymol, Triethanolamine, Triethyl Citrate, Saccharin, diatomaceous earth, ethylene glycol, one or more Cellosolves, aliphatic hydrocharbons, aromatic hydrocarbons, pigments, dyes, phosphates, phosphonates, phosphate esters, phosphinics, and Zinc Oxide, either alone, or more typically, in combination.

Ferrate(VI) can be combined with other sterilizing agents, for example with glutaraldehyde, ortho-phthaldehyde, 1-Hexadecylpyridinium chloride monohydrate, Chlorhexidine, Chlorhexidine Acetate, Chlorobutanol, Chlorocresol, Ethylparaben, Methylphenol, Phenoxyethanol, paraformaldehyde, bleach, formaldeyde, hypochlorite, peroxide, ozone, chloro and/or bromo isocyanuric acid(s), copper ion, calcium hypochlorite, and cetrimide. Some of these sterilizing agents would be more stable in the presence of ferrate(VI) than others. For example, hypochlorite, bleach, and 1-Hexadecylpyridinium chloride monohydrate are stable in the presence of ferrate(VI) but paraformaldehyde and formaldeyde would be oxidized by ferrate(VI) and so would be less compatible.

Some nonlimiting of consumer products include, for example: a skin care lotion comprising one or more of a moisturizer, an antioxidant blend, vitamins E, A, and C, glycerin, cetearyl alcohol, petrolatum, mineral oil, ceteareth-20, tocopheryl acetate, magnesium ascorbyl phosphate, retinyl palmitate, dimethicone, cyclopentasiloxane, glyceryl dilaurate, lecithin, stearic acid, aluminum starch octenylsuccinate, carbomer, methylparaben, propylparaben, alcohol, DMDM hydantoin, sodium hydroxide, and fragrance; a hair conditioner comprising one or more of cetrimonium chloride, Quaterium-18, potassium chloride, disodium EDTA, TEA-dodecylbenzenesulfonate, ascorbic acid, tocophenyl ethyl ether, methylchloroisothiazolinone, hydrolyzed wheat protein, hydrolyzed soy protein, and methylisothiazolinone; a hair shampoo comprising one or more of sodium laureth sulfate, sodium lauryl sulfate, cocamidopropyl betaine, sodium chloride, citric acid, sodium citrate, passiflora incarnata flower extract, anthemis nobilus flower extract, and PEG-60.

For some applications, it is desirable to include a metal ion ligand, or blend of ligands, where "ligand" refers to the normal inorganic chemistry terminology as any ion, atom or molecule that bonds (or "coordinates") to a metal ion, in this case to the ferrate(VI) products of use giving ferric or ferrous ions. One or more ligands are preferred in the formulation when it is desirable to prevent the ferric and/or ferrous ions from forming a ferric oxide "rust" colored stain in its used and instead render the ferric ion product either water soluble, an easily dispersible solid, and/or essentially colorless. Preferably the ligand is a metal ion complexing ligand, i.e. binding the metal ion at least with one bond, and most preferably a metal ion chelating agent where two or more points from a single molecule bond to the ferric or ferrous ion. And it is preferred to incorporate this ligand along with a ferrate treatment during use. Collectively these compounds are referred to as ligands. Preferred are those ligands that result in solubilization of ferric iron, and most preferred are those ligands that also buffer the pH. Ligands also buffer the free metal ion activities in aqueous solution, aqueous-based foams or emulsions, in thin moist films, and the like. The metal ion complexing ligand can be applied before, during, or after a ferrate treatment. In some embodiments, the chelating agent is present in a ferrate composition. Chelating agents that form coordinate covalent bonds to and chelate $Fe^{III}$ ions are especially preferred. This solubilization of iron by ligands can be especially desirable to prevent rust stains. Desferriferrioxamine B, aminocarboxylates such as EDTA, HEDTA, CDTA, NTA, glycine, and the like, hydroxamic acids, catecholates, mono, di and tricarboxylic acids such as malonic acid, citric acid, succinic acid (least preferred due to the weak metal ion complexing nature of this ion), tartaric acids, gluconic acid, oxalic acid, amino phosphonate compounds, Dequest 2010™ and other oxidation resistant chelating phosphonates, and the like are examples of chelating agents capable of strongly solubilizing ferric ion. Alkyl and alkylamino phosphonates, such as HEDP (Dequest 2010®) are most preferred.

Particularly desirable ligand and pH buffering components in some ferrate(VI) compositions are mono, di, tri, tetra, penta, meta, or poly phosphates, phosphonates, and/or phosphinic compounds used singularly or in any combination. Especially preferred is orthophosphate ($PO_4^{3-}$), phosphonate ($HPO_3^{=}$), and phosphinates ($H_2PO_2^{-}$), including their acids, salts and esters, including its protonated forms, i.e. monobasic ($H_2PO_4^{3-}$), dibasic $HPO_4^{2-}$ or tribasic forms, as well as phosphoric acid, and/or polyphosphates and phosphate glasses. Phosphates are most preferred because they are already fully oxidized and therefore immune to further oxidation. On the other hand, sterically hindered phosphonates and phosphinics are also effective where such steric hindrance groups are provided by alkyl, alky lauryl, and/or aryl groups; collectively referred to as "R" groups. R groups can be linear and/or branched hydrocarbons of one to 40 carbons total, although normally each R group would contain no more than 18 carbons. An oxidatively resistant phosphonate example is Dequest® 2010. Many pH buffers do not bond to metal ions and so are not ligands. Such compounds are still useful in the invention as pH buffers, normally present at least in part in acidic form to neutralize the hydroxide ions formed during the reactions, for example bleaching reactions, provided by ferrate.

The function of a pH buffer or metal ion ligand are several. These functions will be illustrated using orthophosphate ion to illustrate. First, only white or colorless species are formed. In aqueous environments, including bulk water, films, foams, emulsions, etc. environments, light purple ferric iron, $Fe^{3+}$, hydrolyzes strongly to form "oxyhydroxy" ferric species, such as FeOOH, $Fe(OH)_2^{4+}$, $Fe_2O_3$, $Fe_3O_4$, and the like, which are yellow, orange, red, black, and/or brown compounds, including mixtures and variations of these colors, known in the terminology of whitening or bleaching as color bodies, or stains. Extensive hydrolysis leads to formation of solid precipitates of stains or adherent surface scales, or inclusions held within the porosity of materials, corresponding to ferric oxyhydroxy solids to precipitate as colored deposits often orange, rust brown, yellow, or black in color. Spectroscopically this color is seen in the UV/Visible spectrum as electronic absorption bands in the visible range, or tailing from the UV into the visible range. To any one skilled in the art of UV/Visible spectroscopy of ferric compounds such electronic absorption bands corresponds to ligand to metal charge transfer bands $CT_{M\_L}$ electronic transitions. Hence the ligand bonded to the ferric ion plays an important role in the color of the compounds it forms. Such compounds and bonds impart color, and usually substantial color to the compound providing the spectrum. This residual solids and color concerns are important when ferrate(VI) is used to bleach surfaces such as teeth, counter tops, etc. The invention prevents such problems by including, in a preferred case, the ligand component or components described above. In the example, phosphate ion prevents the formation of color bodies or formation of adherent ferric-based oxyhydroxy precipitates by complexing the ferric ion that is formed from the reduced ferric iron as it forms, after it forms, or both. It has been found that such ferrate-phosphate mixtures and/or solutions tend not to result in rust colored product mixtures when the ferrate(VI) has been reduced to ferric ions upon the bleaching reaction. In addition, the ferric ions formed from the ferrate(VI) bleaching reactions do not deposit as hard (i.e. adherent) scale on surfaces. Though we do not choose to be held to particular theories, or that such theories limit the extent of the invention, we do offer the explanation for this observation as follows. When ferric ion forms, the ligand, orthophosphate ion in the current case, coordinatively bonds to the ferric bond in place of any oxyhydroxy bonds that would otherwise form. The ferric-phosphate bond also contains $CT_{M\_L}$ electronic transitions but these are located well within the UV band and do not extend appreciably into the visible portion of the spectrum The phosphate-ferric ion bond is also stronger, especially below pH 8, and thereby renders such ferric/phosphate mixtures essentially colorless, and any associated solids colorless or white, and nonadherent to surfaces.

Second, phosphate buffers the pH, resulting in reaction mixtures that can develop strongly acidic, mildly acidic, essentially neutral, mildly basic, or strongly basic reaction mixtures with ferrate. As ferrate's oxidation potential, and therefore reactivity aggressiveness increases with decreasing pH, this use of buffers offers a means to tune the reactivity to the bleaching job needed, to prevent harsh conditions in the cases where skin contact is involved, to impart selective or mild reactivity, and the like. The reactivity of ferrate(VI) can also be varied during the course of a reaction by using conditions allowing pH to vary, i.e. drift up or drift down, during the course of the bleaching or other oxidation reaction.

Thirdly, by forming a ferric phosphate salt particulate, the ferric product is rendered white and nonadherent to the surface. Hence, as in the case of whitening toothpaste, the bleaching reaction results in fine ferric phosphate particulate that is easily rinsed from the mouth along with the normal dentifrice abrasive used in teeth cleaning such as silica or calcium phosphates.

Forth, phosphates can be used to encapsulate the reactive ferrate(VI) ion for storage and reactivity control reasons. For example, potassium ferrate(VI) can be coated with an alkaline alkali or aluminum phosphate or carbonate, for example $K_2HPO_4$, $KHCO_3$, $K_3PO_4$, $K_2CO_3$, alkaline phossy glass, and the like, including mixtures and blends of these. On contact with water, the water soluble phosphate dissolves away releasing the ferrate(VI) and the phosphate buffer, complexing agent, and/or precipitant into the reaction mixture which binds with the ferric ion produced by the action of ferrate(VI) in the whitening or stain removal application.

Preferred counter ions for phosphates include K, Na, $NH_4^+$, $H^+$, Mg, Zn, Ca, and Al.

Ferrate can be formulated with other materials for any of several reasons. First, it provides the ferrate(VI) in a matrix that can be applied to the substrate of interest (grape stained teeth in one example, grape stained fabric or ceramic in a second sample). Secondly, for long shelf-life applications, the formulation contains conditions that do not significantly reduce the stability of the ferrate(VI) salt and protects it from environmental effects that can reduce the stability of ferrate, for example moist atmospheric carbon dioxide. Thirdly, it may contain one or more other components well known in the art to aid cleaning such as soaps, surfactants, emulsifiers, emollients, pH buffer system, dispersant, abrasives, wetting agents, disinfectants other than ferrate(VI), combination of these, and the like. These may be formulated with the ferrate, or added together at the point of use, or at the point of release from their containers.

A particularly preferred formulation is the blending of ferrate(VI) with oxidatively resistant quaternary ammonium salts, preferably surfactants or phase transfer catalyst(s), including those in where the stability is due to steric hindrance, ring stability, or compound insolubility in water, compounds based on quaternary ammonium salts, are particularly effective against stains. Two most preferred quaternary ammonium salts of the invention include Aliquat® 134 or N-methyl tri(n-octyl)ammonium ion and 1-Hexadecylpyridinium chloride monohydrate. These cationic co-reagent or "phase transfer catalyst" ion pairs with the anionic ferrate(VI) to bring it into nonaqueous, and other nonpolar media, pores, and materials where there ferrate(VI) then can oxidize stain causing color bodies. Phosphate precipitating buffer present in such formulations bind to the ferric iron product preventing a ferric rust stain from forming.

Formulations for whitening (or "bleaching") should contain an effective amount of ferrate(VI); that is, an amount sufficient to result in noticeably reducing the color bodies that produce stains after one or more treatments. The amount of ferrate used will vary depending if the treatment is to be achieved quickly or gradually, for example in one, two, three, a few, several, or after many treatments. These treatments, for example to whiten teeth, can be sequential being separated by seconds, minutes, hours, days or weeks and months. Normally the shorter times are normally reserved for highly stained conditions or professional dentistry, while the more separated times are for maintenance of low stained conditions or by applications by the consumer.

The formulation containing ferrate(VI) can optionally contain a cationic phase transfer catalyst for enhanced stain removal in cases where the stain has little or no water solubility. Examples of phase transfer catalysts include quaternary ammonium ions and other oil soluble oxidation resistant cations. Preferred phase transfer catalysts have hydrophobic and hydrophilic moieties in the same molecule, are soluble in aqueous solutions and yet have high oil/water partition coefficients. One preferred type of phase transfer catalyst is a quaternary ammonium ion, more preferably a tetraorganoammonium and/or alkyl phosphonium compound, preferably having a total carbon number of 4 or greater. The organo group can be a straight chain alkyl (such as four n-butyl, or one n-octyl to n-tetradecyl and the other three methyl), but could be branched chain, and/or include aromatic groups, such as phenyl and benzyl groups. The C1 to C4 R groups (4-18 total carbons, including both straight and branched chain) are also effective. Additional groups may also be present in the phase transfer catalyst, such as halogens, nitro groups, pseudo halogens, etc. provided that the final compound possesses a positive net molecular charge, positive in the case of quats, and so long as the oil/water partition coefficient is still large enough to affect the desired reaction rate enhancements via catalysis of solubility. Examples of tetraorganoammonium phase transfer catalysts include $Br^-$, I, $CH_3COO^-$, phthalate, perchlorate, chromate, permanganate, fluoride, nitrate, hydrogen sulfate, methanesulfonate, nitrite, fluoroborate, fluorophosphate, trifluoroacetate, sulfate, carbonate, bicarbonate, monocarboxylate, dicarboxylate, tricarboxylate, hydroxide, and/or Cl⁻ salts of the cations: $^{\oplus}NEt_3(C_4H_9)$, $^{\oplus}N(C_4H_9)_3Et$, $^{\oplus}N(C_4H_9)_3Me$, $(C_6H_5CH_2)N^{\oplus}Et_3$, $(C_6H_5CH_2)N^{\oplus}Me_3$, $(C_4H_9)_4N^{\oplus}$, $^{\oplus}N(C_8H_{17})_3Me$, 1-hexadecylpyridinium chloride monohydrate and $(C_{16}H_{33})N^{\oplus}Me_3$. Other suitable phase transfer catalysts for anionic reactants include: quaternary arsonium salts (such as $AsPh_4^+$), quaternary phosphonium salts, preferably tetraorganophosphonium salts such as $^{\oplus}P(Ph)_4$, $^{\oplus}P(Ph)_3R$ (where R is an alkyl such as methyl, ethyl, propyl or butyl), $^{\oplus}P(C_4H_9)_4$, and organo carboxylics (e.g. organo cobaltic complexes, for example Co(naphthenate)$_2^{\oplus}$ and the like). Less preferred ion pairing phase transfer catalysts include lignosulfonates, and sulfate, dibasic phosphate, due to their low partition coefficients. Co-catalysts may be present and can include species such as alcohols (preferably diols) and zwitterions. Phase transfer catalysts are known in the art and various reviews are available, such as, "Phase Transfer Catalysis: Fundamentals, Applications, and Industrial Perspectives", by C. M. Starks, C. L. Liotta, and M. Halpern, Chapman & Hall, 1994. Neutral complexing molecules such as polyethylene glycol, cryptands, crown ethers (for example, dicyclohexano-18-crown-6, dibenzo-18-crown-6, 18-crown-6, and 15-crown-6) and cyclodextrins can also be used as phase transfer catalysts where the cation for ferrate(VI) is an alkaline metal ion such as K or Na.

The activity of ferrate(VI) is pH dependent, therefore, ferrate(VI) compositions may contain a pH modifier as was described above. Suitable buffers are optional and include alkali, alkaline earth, ammonium, zinc, lanthanide, aluminum, salts, alone and in combination, of one or more anions of bicarbonate, phosphates, hydroxide ion, stannate, citrate ion, triethanolammonium, methanolammonium, ethanolammonium, other alcohol amines, alkoxy amines, quaternary ammonium ions (e.g. prepared from aryl and/or alkyl groups, for example tetramethylammonium ions, tetraethylammonium ions, trimethyl benzylammonium ions, trimethyl dodecylammonium ion and other such fungicides and cationic surfactants, and the like, alone or in combination), zwitterionic ions (such as betaines, N-alkylated betaines, and the like, alone or in combination), chloride ion and combinations thereof. Preferably, unless insolubility is the method of storage, the pH of ferrate(VI) formulations are in the range of >9 pH adjusting agents, if present, are generally present in an amount of up to about 10%, and more preferably from about 0.05% to about 50%, by weight of the formulation, but can rise to over 90%.

Ferrate(VI) can be protected from moisture and/or carbon dioxide by incorporation into a matrix material. A suitable matrix material can be selected from matrix materials known in the art. In some preferred embodiments, the matrix material is an aqueous gel. The level of gelling agent to form a gel composition is from about 0.05% to about 30%, more preferably from about 0.5% to about 20% by weight of the formulation. Suitable gelling agents include carboxypolymethylene, carboxymethyl cellulose, carboxypropyl cellulose, poloxamer, carrageenan, carboxyvinyl polymers, and natural gums and mixtures thereof. Preferred ferrate(VI) formulation materials and matrices are those that either are oxidation resistant and/or render the ferrate(VI) too insoluble to react during storage with the formulation matrix. A particularly preferred matrix material is a hydrophobic material into which ferrate salts can be encased or coated for protection against environmental exposure, especially humid air containing acidic gases, especially carbon dioxide gas. Dried ferrate(VI) solid material is stable in dry air, especially in dry air with little or no $CO_2$ gas present. We found ferrate(VI) to be unreactive in nonpolar media, such as oils, solvents, waxes, and the like. Thus, examples of especially preferred ingredients include hydrocarbon or silicone greases, fluids, waxes, creams, solids, or oils and the like used alone or in combination.

Flavoring can be present in the formulations. The formulations can also include glycerin, sorbitol, xylitol, coloring agents, polyethylene glycol, propylene glycol, and other edible polyhydric alcohols.

Flavors, fragrances, and colorants are often added to consumer and industrial cleaners as an optional but desirable effect during the cleaning, disinfection or bleaching operation. A useful feature of using ferrate(VI) formulations that limit the solubility of ferrate(VI) is the compatibility of this formulation method with other useful additives such as colorants, dyes and pigments, and flavors and fragrances (F&Fs). For example the mint oils, for example spearmint and peppermint, are oil soluble hydroxylated aliphatic hydrocarbons with minimal reactivity exhibited by the alcoholic function. Titanium pigment, dye lakes based on aluminum hydroxide gel, Oil Red O, Food Green 3, and the like, are examples of oxidation resistant and oil soluble or oil dispersible colorants that can be blended with the ferrate/hydrophobic matrix in a consumer formulation. Hence these optional colorants and F&Fs can be dissolved in the hydrophobic matrix for the teeth cleaning hydrocarbon creams, paste, wax, and/or oil, in which the ferrate(VI) active ingredient is insoluble.

The mode of action of the embedded ferrate is believed to be as follows. On water contact the ferrate(VI) is released to accomplish bleaching of teeth, surface being cleaned, or laundry, surface disinfection while the pleasant mint oil fragrance is released in the usual manner into the air surrounding the activity. As the wax, cream, oil, and the like is worked on the surface, for example in a polishing action, the embedded crystals of the water soluble ferrate salt work to the surface and become exposed to the water of the mouth, skin, or water added in the activity, in which it rapidly dissolves where it spontaneously performs the intended bleaching, cleaning, or disinfection action. Other components of the formulation, as described previously regulate the pH, if needed, and prevent unwanted formation of insoluble and stain-like rust by-product.

With the colorants, to enable the use of more easily oxidized additives listed above and others well known in the prior art, the delivery vehicle formulation (oil, wax, cream, etc. matrix) can be "candy stripped" co-extruded so that the materials are not mixed until squeezed or pumped from the storage vessel to the floor, wall, toilet, or teeth scrubbing brush, finger, solution, or other means of applying the ferrate (VI) reagent at the point of use. It is surprising and convenient that a limited amount of skin contact is possible with such a reactive material as ferrate. This seemingly paradoxical observation is unexpected and an embodiment of this invention.

One inventive composition utilizes ferrate particles having an aspect ratio of at least 8 and up to about 30. "Aspect ratio" has the standard definition for particle characterization and means a fiber-like length that is at least 10 times greater than width or thickness, preferably a needle-like morphology with a length at least 10 times that of both width and thickness. The composition can be pure ferrate, for example potassium ferrate(VI), sodium ferrate(VI), barium ferrate(VI), lithium ferrate(VI), and the like, a mixture of high volume or weight percent ferrate(VI) particles and other particles, either intended or byproducts, or ferrate(VI) particles dispersed in a matrix comprising any of the materials discussed herein used alone or in any combination.

Binder materials are useful to hold formulated solid products in the shape of objects that are easily used by the consumer, for example tablets, lozenges, granules, sheets or films, pellets, pills, and the like. Oxidation resistant binders are preferred for constructing and holding ferrate(VI) formulations into such objects, such as chopped and micro fibers of fiberglass, wollastonite, tobomorite, talc, mica, diatomaceous earth, milled fiberglass, calcite, chalk, lime, titania, magnesia, slaked lime, and the like.

Ferrate(VI) can also be added to cement compositions. For example, ferrate(VI) compositions may contain Dequest™, wollastonite, or tobomorite. Ferrate(VI) could aid the adhesion of concrete to the rebar in reinforced concrete. The alkaline concrete matrix could be friendly to ferrate, allowing it sufficient time to react with the rebar.

The invention also provides ferrate(VI) compositions for clearing drains, sewers, or chemical process, biological, food, bioprocessing, agricultural drainage lines, and the like clogged with organic and other materials. For the purposes of simplicity in the following discussion, the conduit in these applications will be collectively referred to as "drains". Likewise, the invention provides a method of clearing drains by applying a ferrate(VI) composition onto a partly or completely clogged drain (including applying to water over a clogged drain). An advantage of using ferrate(VI) is that it is compatible with polyvinyl chloride (PVC) and iron pipes, unlike chlorine-based products or products containing aggressive solvents. Neat powder or granules of sodium ferrate(VI) or potassium ferrate(VI) are effective. The compositions can include a caustic agent, for example, any of the caustic reagents that are known for clearing drains—it is contemplated that the ferrate(VI) will react synergistically with caustic reagents. An effective composition of matter for drain declogging is sodium ferrate(VI) crystals of 1-40 wt % in a aqueous matrix of 25-55 wt % NaOH, and preferably 5-25% sodium ferrate(VI) in a matrix of about 38-55% NaOH, and most preferably 10-20% sodium ferrate(VI) in a matrix of 45-52% NaOH, with the balance of the weight being water. Unexpectedly we found that sodium ferrate(VI), normally exhibits a poor shelf life in the presence of any moisture at all. However, these compositions of matter are stable for many weeks to months if kept away from the carbon dioxide of the air, and longer if refrigerated or frozen. Additional water can be optionally added before, during or after treatment of the clogged drain or sewer. After treatment the drain and/or sewer is flushed with excess water to complete the treatment without concerns for negative environmental impact or negative impact of septic tanks, sewer lines, waste water treatment plants, etc.

The chemistry of the clearing of such piping and drains is believed to be accomplished by the invention through a unique combination of effects of a powerful oxidant, oxygen gas evolution agitation, coagulation and densification of slimes, oxidatively conversion of carbohydrates and cellulosic materials into water soluble and/or dispersible anionic carboxylate ions, heat generation, caustic-based dissolution and hydrolysis of biological materials such as proteins, fats and greases driven by the chemical heat generation. A benefit of the lack of corrosivity of the formulation composition is that the treatment can be allowed to occur for hours, and thereby achieving more cleaning and deplugging per amount of chemicals used. This later effect increases the efficiency and therefore the cost of performing the declogging operation. The declogging formulation can optionally include oxidatively resistant wetting agents and detergents. Alkyl benzene sulfonates, alkylarylsulfonates, and other oxidation resistant wetting agents are preferred.

In a further aspect, the invention provides a cleaning formulation, comprising: a matrix material; and ferrate(VI) dispersed in the matrix material. The matrix material comprises any of the components discussed herein. For water insoluble stains, such as coffee stains in a coffee cup, the cleaning composition preferably includes a cationic phase transfer catalyst described previously. Oxidation resistant wetting agents and detergents are generally preferred as part of the ferrate(VI) formulations for these applications.

Ferrate-containing cleaning compositions may contain an abrasive (and, optionally, a phase transfer catalyst). Mild to hard abrasives are effective and are selected to be most suitable for the cleaning task at hand. Suitable abrasives can be selected from silica, talc, diatomaceous earth, alumina, carbides, pumice, starch, hardened/crystalline plastics such as in "Scotch Brite" pads, and the like, and combinations of these. Other known abrasives can also be used as all abrasives are oxidation resistant.

The invention also provides methods of cleaning eating, medical, tools, and other utensils where clean, disinfected water is unavailable, for example during disaster relief, camping mess kits, field-deployed military forces, refugee camps, slums, situations around broken municipal water mains, situations around municipalities with poor or contaminated water supplies, E. coli, Typhoid, or other bacterial, viral, etc., contaminated foods, potable or other water, and the like. This method includes scouring the eating utensils, etc. with a powder and/or washing the utensils with a ferrate(VI) aqueous solution composition. The ferrate(VI) reacts within seconds to 30 minutes to disinfect the utensils and hands and/or gloves, and then the spent wash solution and can be discarded simply by pouring into a water stream, ditch, river, lake, etc., or onto the ground, or other such readily available location, harmlessly. This composition can include any of the materials described herein, but preferably comprises at least a powder or granules of a water soluble ferrate(VI) salt, or a hydrocarbon wax "soap" bar impregnated with ferrate(VI) salt particulates, and most preferably also containing a soap and/or surfactant, for example hydrolyzed tallow soap, or lauryl sulfonate, and the like. Other soaps or detergents could be combined or substituted for these. Optionally, colorants to characterize the ferrate bar could be added or the bar could naturally reflect the dark purple/black of ferrate(VI) salts. The bar could also contain one or more of the above-described pH buffers to extend the life of the ferrate(VI) during the scrubbing operation by insuring the pH of the operation to be in the 8 to 12 range. The bar could also contain a fragrance and/or ingredients to moisturize and/or soften skin for added comfort from use. These ingredients can be kept separate from each other in the bar by using microemulsion and encapsulation technology already known in the industry to soap bar and personal care products manufacturers and formulators. For example, a ferrate powder would be combined with melted, oxidation resistant, essentially reducing agent free, paraffin such that at least 100 ppm ferrate(VI) by weight is dispersed in the liquid, preferably at least 1000 ppm (or 0.1%), and in some embodiments 1-50%, and then the mixture is blended with an liquid, which may or may not contain a small amount of water, under high shear conditions to generate the microemulsion, followed by rapid cooling and molding into bars. In this manner, a substantial portion of the ferrate(VI) is kept within the hydrocarbon wax or oil droplet of the microemulsion, while the surfactants and other ingredients are immobilized, preferably as a solid mass, within the non-hydrocarbon phase of the emulsion. Once such materials are rubbed, cut or scrapped with added water, for example in a bowl, a sink, a stream of water from a hose or faucet, and the like the non-hydrocarbon phase dissolves in the water to produce micelles, which then in turn dissolve the hydrocarbon from the ferrate, then the freed ferrate(VI) dissolves in the water phase to produce the activated disinfection solution. Continued soaking of utensils or manual and/or automatic scrubbing then provides the contact of the disinfecting ferrate, with assistance and synergistic effects from the soaps and/or detergents present, to accomplish the desirable disinfection and cleaning of the utensils, surfaces, hands, and/or gloves. After the scrubbing activity, these devices and/or surfaces can be wiped, allowed to drain and dry, and/or could be rinsed free of the soap chemicals and ferrate(VI) residue and excess, preferably with disinfected water, which could also be made clean using ferrate. For those cases, such as festivals, fairs, carnivals, political conventions, out door music concerts, and the like, the formulated emulsion, or a more liquid form could be provided soaked into dispensable towelets and hand wipes, which are designed to quickly clean hands, faces, etc. then discarded into the portable toilets or trash receptacles.

The invention includes compositions for and methods of topically applying a ferrate(VI) composition onto a human, nonhuman animal, or plant to kill an organism infecting the host. Examples include a dip for cattle, dog wash, removal of hair lice, removing black spot on roses or other plants. For these uses, it may be desirable for the composition to contain a material that enhances contact of ferrate(VI) with the infecting organism or synergistically combine with ferrate. Such materials include terpenes, pyrethrins, lindane, Pentimethalin, Glyphosate, Crotamiton, tetrahydronapthalene, deltamethrin, Permethrin, and the like. A ferrate(VI) composition could be applied in a cream and then a second solution could be applied to activate the ferrate. Ferrate(VI) compositions might also be used to treat insect infestations in homes, bedding, and stagnant water.

The invention also provides a composition and accompanying method for poisoning insects. The composition comprises combining ferrate(VI) with a food that is appealing to insects. This composition is left in an area traversed by insects, insects eat the composition and are killed by the ferrate.

A ferrate(VI) composition can also be used to bleach and/or color hair or remove odors from hair or fur. For example, ferrate(VI) can be combined with ammonia and a hair dye. In addition to ferrate, a formulation for hair or fur may, optionally, include ingredients such as: oils, waxes, humectants (for example, ethers, polyethers, or mono-, di-, or polyhydric alcohols), thickeners (for example, water soluble polyurethanes, or acrylic copolymeric thickeners), surfactants (for example, reaction products of an alcohol with an alkylene oxide such as Beheneth 5 30, Ceteareth 2 100, Ceteth 1 45, and Ceteareth 20; alkoxylated carboxylic acids; sorbitan derivatives; cationic, amphoteric, or zwitterionic surfactants), pH modifiers, inert ingredients (including barrier materials) such as silica, clay, chalk, talc, diatomaceous earth, mica, magnesium oxide, and zinc oxide, abrasives, and gelling agents (such as hydroxyethylcellulose, locust bean gum, maltodextrin, methylcellulose, agar, dextran, dextran sulfate, gelatin, pectin, potassium alginate, sodium carboxymethylchitin, and xanthan gum). Oils known for use in treating hair may be especially desirable. The composition may also include a soap. In some cases, a colorant may be included as may be found in hair coloring compositions.

The invention also comprises a kit for bleaching or highlighting hair comprising a ferrate(VI) composition. The kit may also contain a hair conditioner composition and/or an applicator for use in applying the bleach mixture to the hair. A variety of applicators may be used so long as they are capable of providing streaks or deposits of bleach mixture to the hair in a desired pattern. Typically, the kit would also contain a reagent, such as a sulfite containing reagent, such as sodium sulfite, to fully discharge the ferrate(VI) oxidant in the hair after the desired period of contact. The advantage of ferrate (VI) over peroxide in this application is the more reliable shelf life for the consumer product and faster bleaching action.

Ferrate(VI) compositions may also be used to wash pets and may be especially useful for washing animals, for example dogs that have been sprayed by a skunk or washing reptiles to kill salmonella. The invention includes kits for and methods of using ferrate(VI) for applying to animals. The ferrate(VI) soap emulsions described above are suitable for performing animal cleaning.

The invention also provides a dispenser that comprises a first compartment that contains a ferrate(VI) composition and a second compartment that comprises a material that, when combined with the ferrate(VI) composition, activates the ferrate. For example, the first compartment (Part A in an earlier discussion above) could contain ferrate(VI) in a hydrophobic matrix, and the second compartment (Part B, which could refer to 1 or more additional parts) could contain an organic solvent or detergent/water solution containing micelles and/or vesicle microstructures for removing, by dissolving or extracting, the hydrophobic protective matrix and thus exposing the ferrate. Alternatively, the second compartment could contain a phase transfer catalyst, pH modifier, or any component that extracts or otherwise improves the action of the ferrate. For example Part B chemistry could result in a warming effect due to dissolution heat of reaction, which then melts the hydrocarbon wax and thereby allowing the ferrate(VI) salt crystals to migrate to the surface and dissolve in the aqueous phase and thereby being release to perform the bleaching, disinfection, etc. desirable action. The two or more part design is most preferred in that it offers the advantage of maintaining separate compartments for storage is that the ferrate(VI) and/or second component could be stable when separate but react when combined. Bicomponent devices for personal products are well-known, for example in epoxy glues for home use. There are numerous examples of bicomponent dispensers, some recent examples are shown in U.S. Pat. Nos. 6,773,414, 6,708,847, 6,672,483, and 6,520,377, which are all incorporated herein by reference. Preferably, the dispenser could be operated by pressing a single button, single plunger, the end of a flexible tube (as is used for many tooth pastes, etc. that would simultaneously dispense the two components. Alternatively, the components could be sequentially dispensed from a single dispenser, for example as peroxide catalyst is combined with polyester resin to initiate polymerization. The two components can be mixed inside a nozzle, or inside an attachment container for a garden hose that meters reagent into the major exiting water stream to crops, gardens, etc., or can be separately applied to a surface (typically in a side-by-side fashion) and combined together (such as by mechanical mixing or chemical diffusion) on the surface.

In one embodiment, the invention provides a tooth whitening appliance, comprising at least one or more of: a brush, syringe, mouthpiece or tooth strip; and a formulation comprising ferrate(VI) disposed on the brush, mouthpiece or tooth strip. Mouthpieces, syringes, and tooth strips for applying a tooth whitening formulation are well known in the art.

Any of which could be employed in the present invention. In a preferred embodiment, the formulation comprises flavoring. In some embodiments, the formulation comprises a gel.

The invention also provides a method of bleaching teeth, comprising: providing ferrate(VI) salt alone and/or a formulation comprising ferrate(VI); and applying an effective amount of the formulation comprising ferrate(VI) to the surface of a tooth. In some embodiments, the formulation comprises a gel. In some embodiments, the formulation is coated on the surface of teeth for at least 10 minutes.

In another aspect, the invention provides: a kit for tooth whitening. comprising: a brush, mouthpiece or tooth strip; and a formulation comprising ferrate, i.e. ferrate(VI). In some embodiments, the formulation comprises a gel.

The invention also provides methods to deliver and apply the formulations to accomplish teeth whitening and/or cleaning. Such methods include media such as tooth paste creams or gels, teeth cleaning powder, contact strips of plastics containing encapsulated ferrate(VI) salts and/or emulsions, with those most preferred that rely on activation by moisture present in the saliva. Paintable coatings that are used to manually brush on a coating or a film of ferrate-based formulation, which can be left on the surface of the film to be rinsed off after a hold period, or rinsed off quickly. A formulation or neat potassium salt can be applied by a dentist, a dental technician, and/or applied by the consumer.

A suitable matrix material can be selected from matrix materials known in the art. In some preferred embodiments, the matrix material is an aqueous gel. The level of gelling agent to form a gel composition is from about 0.05% to about 30%, more preferably from about 0.5% to about 20% by weight of the formulation. Suitable gelling agents include carboxypolymethylene, carboxymethyl cellulose, carboxypropyl cellulose, poloxamer, carrageenan, carboxyvinyl polymers, and natural gums and mixtures thereof. Preferred ferrate(VI) formulation materials and matrices are those that either are oxidation resistant and/or render the ferrate(VI) too insoluble to react during storage with the formulation matrix. Thus, some preferred ingredients include hydrocarbon or silicone greases, fluids, waxes, solids, or oils, used alone or in combination. To enable the use of more easily oxidized additives the delivery vehicle formulation can be "candy stripped" co-extruded so that the materials are not mixed until squeezed or pumped from the storage vessel to the brush, finger, solution, or other means of applying the ferrate(VI) reagent at the point of use.

The inventive methods of cleaning (which include whitening, bleaching, deodorizing and destroying bacteria, fungi, viruses, protozoa, molds, and other microorganisms) can be applied to teeth, fabrics, mouths, clothing, carpets, furniture, flooring and wall coverings.

For cleaning clothing, a ferrate(VI) composition can be added in a detergent formulation into a washing machine. A ferrate(VI) composition could also be selectively applied to a stain, such as with a brush or spray or pen. Various fibers may be treated including polyester, silk, cotton, rayon, spandex, nylon, etc.

The ferrate(VI) compositions may also be used to clean (degrease) electronics.

It is contemplated that a ferrate(VI) composition may also be used to treat a person that has been poisoned. For example, immediately after a person has come into skin, eye, ingested, etc. a poison, such as arsenic (As), nerve agent, mustard agent, lead (Pb), mercury (Hg and its salts and solutions), and the like, the person could be given a ferrate(VI) composition. In this case, it may be useful for the ferrate(VI) to be encapsulated with a slowly dissolving material for delayed release, preferably also with ferric oxyhydroxy sorption capability, such as an anion exchange resin beads (as these are not ingestible through the stomach, intestine, or skin linings). It is further contemplated that a composition could be injected subcutaneously in the case of a snake bite. In such emergency cases, the powdered or granulated form is most preferred, and which can be rapidly dispensed from a tear open plastic-lined packet, and directly applied and worked into the wound to rapidly destroy toxins, proteinaceous matter, and other toxic biomolecules and toxins present there.

The invention also provides a method of washing foods, such as fruits, meats, or vegetables in which the meat, fruit or vegetable (such as hamburger, chicken, lettuce, spinach, carrots, apples, etc.) are washed with a ferrate(VI) solution. This is another case where the color change from purple to near colorless or orange, depending on the concentration of ferrate (VI) used in the wash water, lets the user know that the ferrate(VI) is still present in excess needed for disinfection for at least the required time to achieve a healthy level of disinfection, and when the ferrate(VI) has been used up or degraded. In these cases the purple color can be used to guide the monitoring, either by visual observation, or by automatic electronic colorimetric monitoring of the water bath using a suitable colorimetric sensor, with or without a ORP (oxidation reduction potential) sensor, and where the signal is used to control a ferrate(VI) dispenser automatically and/or manually.

Storing ferrate(VI) in a sealed container can be hazardous if moisture or carbon dioxide gets into the container. Then oxygen gas can be released and a dangerous pressure build-up may occur. Therefore, it is desirable for a container that contains a ferrate(VI) composition to have a pressure release valve or be prepared from $O_2$ permeable materials. Containers with pressure release valves are known in the art. One example can be seen in U.S. Pat. No. 4,690,667. $O_2$ permeable plastics are known to the medical industry.

Discussion of Stain Removal:

The application of a pure ferrate salt or mixture of ferrate salts is sufficient to destroy stains that are caused by oxidizable color bodies, especially organic compounds, and most especially organic compounds representing natural materials such as tea, coffee, grape and other fruit juices, that contain tannins, tannic acids, flavones, and other hydroxylated aromatic compounds. Such destruction of these color bodies is initiated on applying water directly or indirectly to the ferrate on the surface to be cleaned, preferably with mixing. The degree of stain removal, especially food stain removal, can be measured using the color space coordinate "b" for the measurement of residual yellow color.

Ferrate is especially useful for the bleaching, removing, or cleaning of stains, preferably stains consisting of oxidizable color bodies, more preferably organic compounds, and most preferably compounds representing color bodies derived from natural materials such as tea, coffee, grape and other fruit juices, and the like that contain tannins, tannic acids, flavinoids, phenolics, catecholates, gallols, and other hydroxylated aromatic compounds.

Ferrate is desirably co-formulated with an oxidation resistant complexing agent such as orthophosphate, and/or with a chelating agent, as a mixture, or as a separate components of a multi-component cleaner. Such formulations enable the ferrate to perform the needed oxidation chemistry but prevent the deposition of the ferric and/or ferrous iron compounds onto the cleaned surface that may form new staining color bodies containing ferric ion that are difficult to remove due to their high thermodynamic and kinetic stability, especially brown rust or insoluble purple, red and/or orange ferric complexes of phenolate and catecholate type coordination complex compounds. Also, most preferably, chelating agent(s) are selected to also be a pH buffer compound, containing both weak and strong acid groups. This capability to controllably add acidity is useful since ferrate can produce strong base as hydroxide ion, OH⁻, if used in large excess over the demand for cleaning. Therefore it can be optionally useful to include a pH stabilizer or buffer and/or acid in the formulation. For example, 1-hydroxyethylinediphosphonic acid (Etridonic Acid) and its salts is a preferred example of such a chelating agent since it is an acid, a pH buffer, a ferric ion chelator, and forms a water soluble complex, lightly yellow color, with ferric ion that is readily rinsed away. It is also oxidation resistant so that it can be co-formulated with ferrate ion to minimize the number of treatment steps.

Oxidizable chelating agents can also be used but these are most effectively introduced after the ferrate has reacted (discharge of purple color) so that the ferrate is not wastefully consumed by oxidizing the chelating agent as well as the stain, and this also results in wasting a portion of the chelating agent. In this manner, ferrate is also effective in destroying chelating agents and thereby decolorizing metal chelates or chelate formers, which are often the cause of staining. For example tannic acid and its salts, Anthocyanidins (a member of the Flavan-3,4-diols) and its salts, and the like, are strong metal ion chelators that also form strong colors in the ionized and/or metal ion chelate form. Chelating agents comprising both phosphonate and carboxylate groups are preferable since these are also pH buffers Amino phosphonates and amino carboxylates, and especially amino phenolates, and their acidic forms, are less attractive due to their ease of oxidation, unless the amine moiety in the compound is oxidation resistant, as it is in pyrrole and pyridine type groups. Amine groups containing chelating acids or anions are functional if they are added immediately after the discharge of ferrate color. Since the ferric iron product reacts rapidly (in seconds to minutes) to form rust or chelate with foodstuff dyes, if it is left free to react, the addition of such post oxidation chelant is most preferably immediately after ferrate color discharge or within several minutes (preferably 10 minutes, more preferably 1 minute or less). The longer the time the post oxidation step chelating agent is added the longer it will take to discharge any color due to ferric ion product such as rust particles or organo complexes with phenolates or catecholates.

Solid solutions with minerals, especially synthetically-made minerals and co-crystallized salts, containing ferrate ion in a range of proportions and weight percents helps the user to administer ferrate for de-staining and/or cleaning in a number of ways. Such materials are described more fully in the Description section above. Benefits for formulating ferrate ion in this manner are several. It helps the physical use of ferrate ion formulations by making small amounts of ferrate easier to handle by increasing its bulk. They also protects the ferrate ion from premature reactions and moisture absorption, and so help provide longer shelf life, robust packaging options, controlled release, and mechanisms for encapsulation. Since most of the bulk of the materials used in forming solid solutions with ferrate ion are very low cost, solid solutions are also a means for lowering the cost of using ferrate for cleaning and de-staining.

Surfactants are also useful in the use of preparing formulations of ferrate for de-staining and cleaning since many materials are not wetted well by water, or contain layers of hydrophobic environmental contaminants such as greases, oils, fats, polycyclic aromatics, waxy compounds, and the like. For porous materials, fabrics, and the like, wettablity is even more important as surface mechanical scrubbing is less effective in wicking the ferrate treatment into the porous and leaching it out again.

In some preferred embodiments, ferrate(VI) is combined with a pH buffer and/or a chelating agent. As previously discussed, some materials can be both a pH buffer and a chelating agent. pH is preferably maintained at 7.5 or greater, preferably 8.0 or greater, and in some embodiments in the range of 7.5 to 9.0. The solution can be formed in situ on a surface or preformulated and applied to a surface. After the ferrate(VI) is partly or fully reacted, the solution is removed from the surface. Preferably, the surface is then rinsed. Also, preferably, the surface is then treated with a chelating agent to remove any residual Fe species.

A specific example of a ferrate-based whitening or bleaching procedure is as follows using the reagents $K_2FeO_4$, with either 0.25 M Etridonic Acid pH buffering chelant, buffered to pH 7 with NaOH, 0.2% SDS SDS is sodium dodecyl sulfate (also known as sodium lauryl sulfonate) surfactant ion, or 0.25 M Dequest 2010, pH buffering chelant, buffered to pH 8 with NaOH, 0.2% SDS (reaction solution.), and rinse water. The procedure is carried out on a surface to be cleaned, such as stained dentures or a denture/tooth dish or tray respectively:

1. Mix 10 mg of $K_2FeO_4$ per mL to 0.25 M Dequest 2010, buffered to pH 8 with NaOH, 0.2% SDS (reaction solution.), mix vigorously for 10 seconds.
2. Apply 1 mL of this solution to the surface (should completely wet the surface)
3. Continue mixing for a total of about 5 minutes
4. Rinse thoroughly water
5. Apply a solution of 0.25 M Dequest 2010, buffered to pH 7 with NaOH 0.2% SDS (quench solution.).
6. Rinse for another five minutes or more, but not longer than 45 min.
7. Rinse thoroughly with water

EXAMPLE 1

Thermal and Shelf Life Stability of Potassium Ferrate(VI) $K_2FeO_4$ Thermal Stability Test Results The thermal stability of $K_2FeO_4$ was studied in accordance with MIL Spec AR 70-38 Sec. II, 2-4 (hot, dry climate), Table 2-2 (Storage and Transit Conditions) was studied. The required temperature profile appears in FIG. 1.

According to U.S. Army Regulation (AR) 38-70, testing at the highest temperature level (71° C.) in lieu of temperature cycling is acceptable. The more demanding isothermal test conditions were chosen for the preliminary viability assessment testing. In this series of tests, a Blue M Electric Oven, Model OV-490A-3 (S/N OV-11311, BMI No. N-00154, 120V Single Phase, 38-260° C.), was used. The oven was set to maintain an air temperature of approximately 71.5° C. A mercury thermometer immersed in silicone oil was added to the oven for manual tracking of the temperature, and a HOBO model H08-002-02 external temperature logger (Onset Computer Corp., S/N 5948-9820) was used for automated temperature data acquisition. Four ~1.0 g samples of $K_2FeO_4$ TG were transferred to clean 12 mL glass vials with Teflon-lined caps; these samples with purity from ~75-93% were chosen specifically to represent a variety of initial purity values. Before closure, the headspace of each vial briefly was purged (~20 sec at ~250 cm³ (STP)) with ultra-high purity (UHP) argon gas to minimize trapped moisture.

The samples were removed from the oven at 1, 2, 5, 7, 12, 27, 48, and 98 days. The purity of each sample was determined by the technique described in Section 3.2.1. Each vial was assayed three times at each sampling point in order to calculate standard deviation and provide an estimate of precision. When returning the vials to the isothermal oven, the headspace of each vial was purged briefly with UHP argon, as before.

The cycling temperature profile specified in AR 70-38 also was studied. An oven (Fisher Scientific model No. 48) was outfitted with a programmable temperature controller (Omega Engineering model CN3251) and a small fan in order to provide air circulation. Temperature data acquisition was performed using a HOBO data logger (Onset Computer Corp., model HTEA −39+123° C.). The temperature controller was programmed to meet the specifications of AR 70-38 Sec. II, Table 2-2 (Storage and Transit Conditions). Specifically, the oven was programmed to remain above 66° C. for at least 5 hrs and to reach a peak temperature of 71° C. for not more than 1 hr. The programmed parameters appear below in Table 1.

TABLE 1

Cycling Oven Programmed Parameters

| Clock Time | Programmed Induced Air Temperature (° C.) |
|---|---|
| 0:00 | 35 |
| 6:30 | 35 |
| 12:30 | 66 |
| 15:00 | 71 |
| 17:30 | 66 |
| 23:30 | 35 |

EXAMPLE 2

Stain Removal from Calcium Deficient Hydroxy Apatite Disks (Human Tooth Model) Using Potassium Ferrate(VI)

Tea staining Solution: 200 mL of high-purity deionized (HPDI) water was heated to boiling in a 500-mL beaker. The beaker was removed from heat and 4 Lipton™ tea bags were added. The tea bags were allowed to soak for 5 minutes. The tea bags were pressed with a spatµLa upon removal to remove liquid. The tea was allowed to cool to room temperature whereupon heavy turbidity occured.

Tea staining Procedure: A calcium-deficient hydroxyapatite (HAP) disk (Clarkson Chromatography Products) was placed into a 50-mL centrifuge tube with 10 mL of tea solution. The centrifuge tube was gently shaken by hand for 15 minutes. The tea solution was decanted and replaced with 10 mL of HPDI water and vortexed for 30 seconds. The water was decanted and replaced with 10 additional mL of HPDI water and vortexed for 30 seconds. The disk was removed with forceps and patted dry with a tissue. The disk was allowed to air dry at room temperature for at least one hour. Color Space coordinate readings were found to be $L^*=103.3$ lightness/darkness); $a^*=-2.8$ (blue/red); and $b^*=-3.7$ (yellow/green) for the unstained disc. The reflectance of visible light was recorded as 112.352 at 450 nm, and 101.312 at 750 nm respectively for the unstained disc. $\Delta E=21.35$; $L^*=84.7$ (lightness/darkness); $a^*=5.5$ (blue/red); and $b^*=2.7$ (yellow/green) for the stained disc. The reflectance of visible light was recorded as 61.768 at 450 nm, and 85.023 at 750 nm respectively for the stained disk. The unstained disc appeared pure white and the stained disc a medium brown color.

Oxidation resistant chelating buffer: 0.25M 1-Hydroxyethylidenediphosphonic acid (etridonic acid) (Dequest® 2010, Thermphos) (HEPA) was pH adjusted by microtitration with 10N NaOH. 1.28 g of 1-Hydroxyethylidenediphosphonic acid was to a 25-mL volumetric flask and brought to volume with HPDI water. The solution was transferred to a 50-mL beaker with a stir bar and pH adjusted using 10.04N NaOH, monitored with a calibrated pH meter. Aliquat 336® (Cognis) (also suitable is Aliquat 134®) (N-methyl-tri-(n-octyl)ammonium chloride), (N-methyl TOA) or "HEPA" chelating pH Buffer: 2.5-µL of N-methyl TOA was added to 5 mL of pH 7 HEPA buffer and sonicated for 1 minute. pH 7 Sodium Dodecyl Sulfate (SDS)/HEPA Buffer: 10 mg of SDS was added to 5 mL of pH 7 HEPA buffer and sonicated for 1 minute. pH 8 SDS/HEPA Buffer: 10 mg of SDS was added to 5 mL of pH 8 HEPA buffer and sonicated for 1 minute.

Calcium Deficient Hydroxyapatite (HAP) Disk Examples:

A. A tea stained disk was placed into the bowl of the bowl of a watch glass and 100 µL of pH 7 HEPA buffer was pipetted onto the disk surface. 3.7 mg of potassium ferrate(VI) was added to the disk surface and mixed gently. The surface liquid appeared black. The color changed to amber in about 4 minutes with red particles suspended in the liquid. The disk was rinsed at 10 minutes with HPDI water. The disk was stained purple with rust stains. Color Space coordinate readings were found to be $\Delta E$ (versus tea stain)=13.57; $L^*=72$ (lightness/darkness); $a^*=2.6$ (blue/red); and $b^*=-1.1$ (yellow/green). The reflectance of visible light was recorded as 44.547 at 450 nm, and 61.521 at 750 nm respectively.

Observation: Rust stains, possibly from direct deposition of rust formed by chemical reduction of ferrate(VI) when it oxidizes organic stain-forming color bodies, such as the tannins, and the like of tea and other foods.

B. A tea stained disk was placed into a 50 mL centrifuge tube. 1 mL of pH 7 HEPA buffer was added followed by 9 mL of HPDI water. 9.7 mg of potassium ferrate(VI) was added. The tube was gently hand shaken for 10 minutes. The disk was removed and rinsed with HPDI water. The disk was stained purple with rust stains. Color Space coordinate readings were found to be $\Delta E$ (versus tea stain)=8.29; $L^*=79.1$ (lightness/darkness); $a^*=1.6$ (blue/red); and $b^*=-2$ (yellow/green). The reflectance of visible light was recorded as 57.457 at 450 nm, and 69.889 at 750 nm respectively.

Observation: Rust stain formation, possibly from precipitation of brown ferric hydroxide formed from reduction of ferrate(VI) during the de-staining reaction (consistent with "b" values). This result supported the contention, validated in the testing below, that rust stains can be prevented by providing a solubilizing and/or ferric ion bleaching agent in the formulation along with the ferrate (VI) ion. Hence the most preferred such complexing agent would also be oxidation resistant, at least for the duration of the oxidation reaction with ferrate(VI).

C. 10 mg of potassium ferrate(VI) was added to 1 mL of pH 7 HEPA buffer in a 50 mL centrifuge tube. 9 mL HPDI water was added, and the solution was shaken for a few seconds followed by the addition of a tea stained HAP disk. The disk was removed at 10 minutes and rinsed with HPDI water. The disk was stained purple.

Observation: Discovery and Confirmation that solubilization and chelation control of ferrate(III) in solution, produced from ferrate(VI) during destaining, prevents or at least minimizes rust staining. Hence ferrate(VI) is shown here, and further below, that it can be used to destroy stains, especially problematic food stains such as tea, coffee, grape juice, cranberry juice, and the like, without the formation of rust stain from the iron product.

D. An unstained HAP disk was placed into the bowl of a watch glass and 100 µL of pH 7 HEPA buffer was pipetted onto the disk surface. It was observed that the pH 7 HEPA buffer does not absorb into disk as HPDI water does. 1.3 mg of potassium ferrate(VI) added and mixed into the solution. The liquid turned from purple to brown in about 2 minutes. The disk had a very slight yellow tint. Color Space coordinate readings were found to be $\Delta E$ (versus tea stain)=_ 20.34; $L^*$=103.4 (lightness/darkness); $a^*$=−2.2 (blue/red); and $b^*$=0.5 (yellow/green). The reflectance of visible light was recorded as 105.246 at 450 nm, and 102.793 at 750 nm respectively.

Observation: Potassium ferrate(VI) used alone does not create a purple color stain.

E. A tea stained disk was placed into the bowl of a watch glass and 100 µL of pH 7 HEPA buffer was pipetted onto the surface. 1.4 mg of potassium ferrate(VI) was added to the disk surface and mixed gently. The surface liquid appeared purple. The reaction was allowed to continue for 5 minutes. The liquid became brown. The disk was rinsed several times with HPDI water. 100 µL of pH 7 HEPA buffer was pipetted onto the disk surface and allowed to react for 5 minutes. The disk was rinsed several times with HDPI water and the color was observed to be lighter purple than previous examples. Color Space coordinate readings were found to be $\Delta E$ (versus unstained disk)=4.24; $L^*$=90.1 (lightness/darkness); $a^*$=1.3 (blue/red); and $b^*$=−2.2 (yellow/green). The reflectance of visible light was recorded as 77.562 at 450 nm, and 87.011 at 750 nm respectively.

Observation: HEPA buffer addition following potassium ferrate(VI) reaction appears to solubilize iron ions thought to be present as iron/tannic acid complexes which form the purple color by forming ferric chelates of catacholate and/or phenolate type bonds that are known to be highly colored either purple, red or orange. The removal of color was possibly also inhibited due to beading as observed in example D (above).

F. A tea stained disk was placed into the bowl of a watch glass and 100 µL of pH 7 HEPA buffer was pipetted onto the surface. One drop of N-methyl TOA was added to the disk surface and mixed causing formation of an emulsion formed. 1 mg of potassium ferrate(VI) was added and mixed into the liquid. The emulsion remained. The color was purple with streaks where mixing occurred. Color Space coordinate readings were found to be $\Delta E$ (versus tea stain)=8.65; $L^*$=77 (lightness/darkness); $a^*$=2.1 (blue/red); and $b^*$=0.7 (yellow/green). The reflectance of visible light was recorded as 44.547 at 450 nm, and 68.873 at 750 nm respectively.

Observation: N-methyl TOA de-staining is not effective at high ratios because a thick emulsion is formed that would need significant mechanical mixing to spread on the surface fully.

G. A tea stained disk was placed into the bowl of a watch glass and 100 µL of N-methyl TOA/HEPA buffer was pipetted onto the disk surface and allowed to soak for 2 minutes. 0.7 mg of potassium ferrate(VI) was added and mixed with a plastic pipette tip for 30 seconds. The color changed from purple to orange in one minute. The disk was rinsed with HPDI water at 5 minutes and patted dry with a tissue, then an additional 100 µL of N-methyl TOA/HEPA buffer was applied and rinsed with HPDi water after 5 minutes. The purple color was removed but brown staining observed. Color Space coordinate readings were found to be $\Delta E$ (versus tea stain)=10.88; $L^*$=94 (lightness/darkness); $a^*$=−0.6 (blue/red); and $b^*$=−0.1 (yellow/green). The reflectance of visible light was recorded as 82.923 at 450 nm, and 92.128 at 750 nm respectively.

Observation: N-methyl TOA at lower concentration allows more complete surface reactions for potassium ferrate (VI) and HEPA.

H. A tea stained disk was placed into the bowl of a watch glass and 100 µL of N-methyl TOA/HEPA buffer was pipetted onto the disk surface and allowed to soak for 3 minutes. 1.3 mg of potassium ferrate(VI) added and mixed with a plastic pipette tip for 30 seconds, then allowed to react for 5 minutes. The disk was rinsed with HPDI water and patted dry with a tissue, then an additional 100 µL of N-methyl TOA/HEPA buffer and allowed to react for 5 minutes followed by an additional 100 µL of N-methyl TOA/HEPA buffer pipetted onto surface and allowed to react for 5 more minutes. The disk was rinsed with HPDI water and appeared a light brown color. Color Space coordinate readings were found to be $\Delta E$ (versus tea stain)=10.06; $L^*$=93.6 (lightness/darkness); $a^*$=1.3 (blue/red); and $b^*$=0.6 (yellow/green). The reflectance of visible light was recorded as 82.479 at 450 nm, and 93.202 at 750 nm respectively.

Observation: additional ferrate(VI) and/or HEPA addition removes more color.

I. A tea stained disk was placed into the bowl of a watch glass and 100 µL of N-methyl TOA/HEPA buffer was pipetted onto the surface and allowed to soak for 3 minutes. 1.3 mg of potassium ferrate(VI) added and mixed with a plastic pipette tip for 30 seconds. The potassium ferrate(VI) did not distribute evenly, decoloring the center and not the edge. The mixture was allowed to react 5 minutes, then was rinsed with HPDI water, followed by addition of 200 µL of N-methyl TOA/HEPA buffer. More decoloring was observed at the center where the potassium ferrate(VI) had contact. Color Space coordinate readings were found to be $\Delta E$ (versus tea stain)=11.69; $L^*$=91.2 (lightness/darkness); $a^*$=−0.8 (blue/red); and $b^*$=−4.7 (yellow/green). The reflectance of visible light was recorded as 83.889 at 450 nm, and 83.121 at 750 nm respectively.

Observation: Surface addition of potassium ferrate(VI) can result in uneven color removal if the ferrate(VI) ion is not completely dissolved and dispersed before it is fully consumed.

J. A tea stained disk was placed into the bowl of a watch glass and 200 µL of N-methyl TOA/HEPA buffer was pipetted onto the disk surface and allowed to soak for 2 minutes. 2.3 mg of potassium ferrate(VI) was added and stirred for 1 minute, then allowed to react for 5 minutes. The disk was rinsed with HPDI water and then an additional 200 µL of N-methyl TOA/HEPA buffer was added and allowed to react for 5 minutes follwoed by rinsing with HPDI water. Rust spots observed where the potassium ferrate(VI) made initial contact. Color Space coordinate readings were found to be $\Delta E$ (versus tea stain)=9.10; $L^*$=87.5 (lightness/darkness); $a^*$=−0.1 (blue/red); and $b^*$=−3.9 (yellow/green). The reflectance of visible light was recorded as 44.547 at 450 nm, and 78.071 at 750 nm respectively. Color Space coordinate readings were found to be $\Delta E$ (versus tea stain)=9.10; $L^*$=87.5 (lightness/darkness); $a^*$=−0.1 (blue/red); and $b^*$=−3.9 (yellow/green). The reflectance of visible light was recorded as 44.547 at 450 nm, and 78.071 at 750 nm respectively.

Observation: Surface addition of excess potassium ferrate (VI) can cause rust staining if neat potassium ferrate(VI) contacts the surface of the disk. Color moved through the disk during rinses showing the importance of being able to destain internal pores, as is provided by the invention.

K. A tea stained disk was placed into the bowl of a watch glass. 1 mL of N-methyl TOA/HEPA buffer was mixed with 9.9 mg of potassium ferrate(VI) for 10 seconds in a 10 mL beaker. The solution was pipetted onto a HAP disk so that the disk was fully covered in liquid. The solution was allowed to react for 10 minutes. The disk color changed from purple to brown with particulates suspended in the solution. The disk was removed, rinsed with HPDI water, and patted dry with a tissue. 400 µL of N-methyl TOA/HEPA buffer was added and allowed to soak for 45 minutes. The disk was rinsed with HPDI water and patted dry with a tissue. Significant color removal was observed. Color Space coordinate readings were found to be $\Delta E$ (versus tea stain)=17.77; $L^*$=100.8 (lightness/darkness); $a^*$=−0.3 (blue/red); and $b^*$=−2.1 (yellow/green). The reflectance of visible light was recorded as 102.827 at 450 nm, and 103.311 at 750 nm respectively.

Observation: Pre-mixing of potassium ferrate(VI) and HEPA buffer combined with submerging the disk in solution allows uniform color removal. Addition of surfactant allows complete surface reaction and penetration of porosity. Longer HEPA buffer and/or water soak removes the iron/tannic acid purple color more completely with surfactant.

L. A tea stained disk was placed into the bowl of a watch glass and 100 µL of pH 7 SDS/HEPA buffer was pipetted onto the disk surface and allowed to soak for 10 minutes. 1.3 mg of potassium ferrate(VI) added and mixed with a plastic pipette tip for 30 seconds then allowed to react for 10 minutes. The disk was rinsed with HPDI water and additional 100 µL of pH 7 SDS/HEPA buffer was added, then rinsed after ten minutes with HPDI water. Most of the color was removed from the center of the disk. Color Space coordinate readings were found to be $\Delta E$ (versus tea stain)=_16.32; $L^*$=99.1 (lightness/darkness); $a^*$=−0.4 (blue/red); and $b^*$=−2.2 (yellow/green). The reflectance of visible light was recorded as 99.384 at 450 nm, and 98.847 at 750 nm respectively.

Observation: SDS surfactant allows more complete color removal than N-methyl TOA; surface treatment results in less uniform color removal than submersion technique.

M, N, and O. Tea stained disks M and N were placed into watch glasses. Disk O was reserved as an untreated control. 3 mL of pH 7 SDS/HEPA buffer was added to 29.3 mg of potassium ferrate(VI) and mixed for 5 seconds. 1 mL of the resulting solution applied to disks M and N. The disks were flipped at 30 seconds, and flipped back at one minute. The disks were removed at 3 minutes and rinsed 10 times with HPDI water then patted dry with a tissue. 400 µL of SDS/HEPA buffer was added to each disk. The disks were flipped at one minute and back at two minutes. The pH 7 SDS/HEPA buffer solution developed a yellow tint. The disks were removed at 8 minutes, rinsed with HPDI water, and placed in fresh pH 7 SDS/HEPA buffer (200 µL). They were allowed to soak for an additional 35 minutes, rinsed with HPDI water, and patted dry with a tissue. An additional HPDI rinse after an hour of drying removed much of the residual purple color from the disk, leaving a brown residue in the watch glass. Color Space coordinate readings for M were found to be $\Delta E$ (versus disk 0)=12.15; $L^*$=100.1 (lightness/darkness); $a^*$=0 (blue/red); and $b^*$=−1.9 (yellow/green). The reflectance of visible light was recorded as 100.820 at 450 nm, and 102.480 at 750 nm respectively. Color Space coordinate readings for N were found to be $\Delta E$ (versus disk O)=12.63; $L^*$=100.6 (lightness/darkness); $a^*$=−0.3 (blue/red); and $b^*$=−1.4 (yellow/green). The reflectance of visible light was recorded as 101.538 at 450 nm, and 101.930 at 750 nm respectively. Color Space coordinate readings for O were found to be $L^*$=88.6 (lightness/darkness); $a^*$=3.3 (blue/red); and $b^*$=0.2 (yellow/green). The reflectance of visible light was recorded as 71.726 at 450 nm, and 86.756 at 750 nm respectively.

Observation: More complete color removal may be achieved by slowing the potassium ferrate(VI) reaction rate by raising the starting pH from 7 to 8 and using complexing agent, and more preferably by using a pH buffer that is also a chelating agent.

P, Q, and R. Tea stained disks were prepared as described above except that they were allowed to soak in the tea solution overnight instead of 15 minutes, resulting in a darker stain. Disk R was reserved as a control. Disks P and Q were placed into watch glasses. 25 mg of potassium ferrate(VI) was added to 1.5 mL pH 8 SDS/HEPA buffer and mixed for 30 seconds in a 10 mL beaker. 0.75 mL of this solution was added to each disk. A deep violet color was observed with a wax-like film on the surface of the liquid. The disks were flipped at 3 minutes. The pH of the solution is 11 or 12 by indicator strips. The disks were removed at 5 minutes and rinsed 5 times per side with HPDI water, then patted dry with a tissue. Brown material was observed moving into the wet portion of disk, so the disks were rinsed an additional 2 times per side with HPDI water, then patted dry with a tissue and placed into watch glass with 1 mL of pH 8 SDS/HEPA buffer. The disks were flipped every 6 minutes. The solution turned yellow with brown particulates. The disks were removed at 45 minutes, rinsed 5 times per side with HPDI water and patted dry. After drying for one hour, disk P was rinsed again with HPDI water Color Space coordinate readings for P were found to be $\Delta E$ (versus disk R)=_25.40; $L^*$=103.5 (lightness/darkness); $a^*$=−2.1 (blue/red); and $b^*$=−3.2 (yellow/green). The reflectance of visible light was recorded as 111.059 at 450 nm, and 103.081 at 750 nm respectively. Color Space coordinate readings for Q were found to be $\Delta E$ (versus disk R)=22.83; $L^*$=101.8 (lightness/darkness); $a^*$=−1.2 (blue/red); and $b^*$=−0.7 (yellow/green). The reflectance of visible light was recorded as 103.784 at 450 nm, and 101.164 at 750 nm respectively. Color Space coordinate readings for R were found to be $L^*$=81.4 (lightness/darkness); $a^*$=7.1 (blue/red); and $b^*$=5.3 (yellow/green). The reflectance of visible light was recorded as 53.054 at 450 nm, and 81.039 at 750 nm respectively.

Observation: Raising the pH to 8 allowed more working time before the ferrate(VI) purple color was expended. Water rinsing following treatment removed more color.

S. Tea stained disk treated the same way as P and Q. (replicate) Color Space coordinate readings for S were found to be $L^*$=99.3 (lightness/darkness); $a^*$=_0 (blue/red); and $b^*$=_−1.7_(yellow/green). The reflectance of visible light was recorded as 98.555 at 450 nm, and 98.659 at 750 nm respectively.

T. A tea stained disk was placed into watch glass. 1 mL of 3% hydrogen peroxide was pipetted onto the disk, followed by 0.5 g of sodium bicarbonate. The solution was mixed by a gloved finger on the disk surface. The solution was decanted and the application was repeated and allowed to react for 5 minutes. The disk was removed and rinsed 5 times per side with HPDI water and then placed into an HPDI water soak for 45 minutes. Much of the color was removed. Disk had a pale yellow-amber tint. Color Space coordinate readings were found to be $\Delta E$ (versus tea stain)=13.44; $L^*$=96.9 (lightness/darkness); $a^*$=0.4 (blue/red); and $b^*$=0.3 (yellow/green). The reflectance of visible light was recorded as 89.892 at 450 nm, and 94.030 at 750 nm respectively.

U. A tea stained disk was treated the same way as P and Q, except disk was submerged in HPDI water for 45 minutes following the pH 8 SDS/HEPA buffer soak instead of allowing it to dry. Color was removed as effectively as with a dried sample. Color Space coordinate readings were found to be ΔE (versus tea stain)=13.44; L*=96.9 (lightness/darkness); a*=0.4 (blue/red); and b*=0.3 (yellow/green). The reflectance of visible light was recorded as 89.892 at 450 nm, and 94.030 at 750 nm respectively.

V. A tea stained disk was placed into the bowl of a watch glass. 1 mL of pH 8 SDS/HEPA buffer was pipetted onto the disk and allowed to soak for 45 minutes. The disk was removed and rinsed 5 times with HPDI water and allowed to air dry for one hour. Very little color change was observed; the color was slightly lighter. Color Space coordinate readings were found to be ΔE (versus tea stain)=2.47; L*=85.7 (lightness/darkness); a*=5 (blue/red); and b*=4.9 (yellow/green). The reflectance of visible light was recorded as 60.814 at 450 nm, and 87.464 at 750 nm respectively.

A-1. A tea stained disk was treated the same way as P and Q except that the 45 minute soak used pH 7 SDS/HEPA buffer.

A-2. A tea stained disk was treated with 30 mg of calcium carbonate and 250 µL of HPDI water. 10 mg of potassium ferrate(VI) was added and the mixture was mixed with a gloved finger tip. The color turned darker orange brown. The disk was rinsed with HPDI water at 5 minutes, but the color was not removed. Color Space coordinate readings were found to be ΔE (versus tea stain)=29.21; L*=69.5 (lightness/darkness); a*=14.4 (blue/red); and b*=26 (yellow/green) The reflectance of visible light was recorded as 22.036 at 450 nm, and 64.152 at 750 nm respectively.

A-3. A tea stained disk was soaked in HPDI water for 45 minutes. No color removal was observed.

A-4. A grape Juice stained disk was treated the same way as P and Q. All stains were removed. Color Space coordinate readings were found to be ΔE (grape juice stain)=6.10; L*=103.5 (lightness/darkness); a*=_−1.9 (blue/red); and b*=−3.1 (yellow/green). The reflectance of visible light was recorded as 111.244 at 450 nm, and 103.795 at 750 nm respectively. Color Space coordinate readings for grape juice stain were found to be L*=98.4 (lightness/darkness); a*=−2.4 (blue/red); and b*=−6.4 (yellow/green) The reflectance of visible light was recorded as 103.842 at 450 nm, and 96.473 at 750 nm respectively.

A-5. A Cran-Grape™ juice stain was treated the same way as P and Q. All stains were removed. Color Space coordinate readings were found to be ΔE (cran-grape juice stain)=6.82; L*=107.3 (lightness/darkness); a*=−3.2 (blue/red); and b*=−5.5 (yellow/green). The reflectance of visible light was recorded as 126.369 at 450 nm, and 108.805 at 750 nm respectively. Color Space coordinate readings for cran-grape juice stain were found to be L*=104.6 (lightness/darkness); a*=2.7 (blue/red); and b*=−3.4 (yellow/green) The reflectance of visible light was recorded as 118.143 at 450 nm, and 111.850 at 750 nm respectively.

A-6. A coffee stained disk was treated the same way as P and Q. All stains were removed. Color Space coordinate readings were found to be ΔE (coffee stain)=13.57; L*=101.9 (lightness/darkness); a*=−2.1 (blue/red); and b*=−2.8 (yellow/green). The reflectance of visible light was recorded as 106.774 at 450 nm, and 99.233 at 750 nm respectively. Color Space coordinate readings for coffee stain were found to be L*=89.7 (lightness/darkness); a*=2.1 (blue/red); and b*=1.4 (yellow/green) The reflectance of visible light was recorded as 73.162 at 450 nm, and 85.120 at 750 nm respectively.

B-1. A tea stained disk was place into the bowl of a watch glass. 10 mg of calcium carbonate and 12 mg of potassium ferrate(VI) added to 2 mL of pH 8 SDS/HEPA buffer and stirred for 30 seconds with a plastic pipette. The solution was pipetted onto the disk. The disk was flipped at 2 minutes and 4 minutes. The disk was removed at 5 minutes, then rinsed 5 times per side with HPDI water and patted dry. The disk was placed in a clean watch glass and 1 mL of pH 8 SDS/HEPA buffer was added. The disk was removed at 45 minutes, rinsed 5 times per side with HPDI water and patted dry. The disk was allowed to air dry for one hour and was then rinsed 3 times with HPDI water. All stains were removed. Color Space coordinate readings were found to be ΔE (versus B-2, tea stained)=15.29; L*=100.8 (lightness/darkness); a*=0.5 (blue/red); and b*=0.1 (yellow/green). The reflectance of visible light was recorded as 100.124 at 450 nm, and 103.677 at 750 nm respectively. Color Space coordinate readings for B-2 stain were found to be L*=87.4 (lightness/darkness); a*=5.5 (blue/red); and b*=5.5 (yellow/green). The reflectance of visible light was recorded as 63.178 at 450 nm, and 84.853 at 750 nm respectively.

The invention claimed is:

1. A toothpaste comprising a cleaning composition, comprising,
   a) ferrate(VI) salt,
   b) a complexing agent;
   c) a pH buffer for controlling the pH to be at least 7 or above; and
   d) an optional phase transfer catalyst;
   wherein the complexing agent, the pH buffer, and the phase transfer catalyst are oxidation resistant.

2. The toothpaste of claim 1 comprising a silica-containing abrasive.

3. A composition for cleaning and/or disinfection, comprising:
   a) ferrate(VI) and a hydrophobic material encapsulating the ferrate, wherein the hydrophobic material is soluble in organic solvents or soaps or detergents in the presence of moisture;
   b) an oxidation resistant complexing agent;
   c) an oxidation resistant pH buffer for controlling the pH to be at least 7 or above; and
   d) an optional oxidation resistant phase transfer catalyst.

4. A chewing gum for cleaning and/or disinfection, comprising:
   a) ferrate(VI) and a hydrophobic material encapsulating the ferrate;
   b) a complexing agent;
   c) a pH buffer for controlling the pH to be at least 7 or above;
   d) an optional phase transfer catalyst; and
   e) an elastomer;
   wherein the complexing agent, the pH buffer, and the phase transfer catalyst are oxidation resistant.

5. A toothpaste comprising the cleaning composition of claim 3 wherein the hydrophobic material is a teeth cleaning hydrocarbon cream, paste, wax, and/or oil.

6. A method of cleaning a tooth comprising applying a composition according to claim 1 to a surface of the tooth.

* * * * *

UNITED STATES PATENT AND TRADEMARK OFFICE
CERTIFICATE OF CORRECTION

PATENT NO. : 8,663,607 B2  Page 1 of 1
APPLICATION NO. : 12/529540
DATED : March 4, 2014
INVENTOR(S) : Monzyk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 784 days.

Signed and Sealed this

Twenty-ninth Day of September, 2015

Michelle K. Lee
*Director of the United States Patent and Trademark Office*